United States Patent
Safar et al.

(10) Patent No.: US 6,287,794 B1
(45) Date of Patent: Sep. 11, 2001

(54) FACTOR VLLA INHIBITORS

(75) Inventors: Pavel Safar; Alena Safarova, both of Tucson, AZ (US); Peter Wildgoose, Oberursel (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/395,572

(22) Filed: Sep. 14, 1999

(30) Foreign Application Priority Data

Sep. 15, 1998 (EP) .................................................. 98117506

(51) Int. Cl.⁷ ............................... C12Q 1/56; C12Q 1/00; A61K 38/00
(52) U.S. Cl. ..................................... 435/13; 435/2; 435/4; 435/7.71; 436/15; 436/69; 530/300; 530/380; 530/381; 530/384; 530/331; 930/250; 514/17
(58) Field of Search .......................... 435/13, 4, 2, 7.71; 436/15, 69; 530/300, 380, 381, 384, 331; 930/250

(56) References Cited

U.S. PATENT DOCUMENTS

| | | | |
|---|---|---|---|
| 5,663,297 | 9/1997 | Alig et al. | 530/331 |
| 5,849,510 | * 12/1998 | Al-Obeidi et al. | 435/13 |

FOREIGN PATENT DOCUMENTS

| | | |
|---|---|---|
| WO 89/09612 | 10/1989 | (WO) . |
| WO 90/03390 | 4/1990 | (WO) . |
| WO 91/07432 | 5/1991 | (WO) . |
| WO 92/06711 | 4/1992 | (WO) . |
| WO 95/00541 | 1/1995 | (WO) . |
| WO 96/12800 | 5/1996 | (WO) . |
| WO 96/40779 | 12/1996 | (WO) . |
| WO 97/47651 | 12/1997 | (WO) . |

OTHER PUBLICATIONS

James A. Ostrem et al., "Discovery of a Novel, Potent, and Specific Family of Factor Xa Inhibitors via Combinatorial Chemistry," Biochemistry, vol. 37, pp. 1053–1059 (1998).

Ronald N. Zuckermann et al. "Efficient Method for the Preparation of Peptoids [Oligo(N–substituted glycines)] by Submonomer Solid–Phase Synthesis," J. Am. Chem. Soc., vol. 114, pp. 10646–10647 (1992).

Peter Sieber, "A New Acid–Labile Anchor Group for the Solid–Phase Synthesis of C–Terminal Peptide Amides by the FMOC Method," Tetrahedron Letters, vol. 28, No. 19, pp. 2107–2110 (1987).

Hans Rink, "Solid–Phase Synthesis of Protected Peptide Fragments Using a Trialkosy–Diphenyl–Methylester Resin," Tetrahedron Letters, vol. 28, No. 33, pp. 3787–3790 (1987).

Michael S. Bernatowicz et al. "A Comparison of Acid Labile Linkage Agents for the Synthesis of Peptide C–Terminal Amides," Tetrahedron Letters, vol. 30, No. 35, pp. 4645–4648 (1989).

Athanassios Giannis et al., "Peptidomimetics for Receptor Ligands–Discovery, Development, and Medical Perspectives," Angew. Chem. Int. Ed. Engl. vol. 32, pp. 1244–1267 (1993).

Laurence A. Harker et al., "Antithrombotic and Antilesion Benefits without Hemorrhagic Risks by inhibiting Tissue Factor Pathway," Haemostasis, vol. 26 (suppl 1), pp. 76–82 (1996).

Claude R. Benedict et al., "Active Site–Blocked Factor Xa Prevents Thrombus Formation in the Coronary Vasculature in Parellel With Inhibition of Extravascular Coagulation in a Canine Thrombosis Model," Blood, vol. 81, No. 8, pp. 2059–2066 (1993).

Laurence A. Harker et al., "Antithrombotic Benefits and Hemorrhagic Risks of Direct Thrombin Antagonist," Thrombosis and Haemostasis, vol. 74 (1), pp. 464–472 (1995).

Toru Yokoyama, PhD.et al., "Antithrombotic Effects of Orally Active Synthetic Antagonist of Activated Factor X in Nonhuman Primates," Circulation, vol. 92, pp. 485–491 (1995).

G. J. Broze, Jr., "Tissue Factor Pathway Inhibitor and the Current Concept of Blood Coagulation," Blood Coagulation and Fibrinolysis, vol. 6, Suppl 1, pp. S7–S13 (1995).

H. Cole, "The Tissue Factor Pathway of Coagulation," Australian Journal of Medical Science, vol. 16 pp. 87–93 (1995).

* cited by examiner

Primary Examiner—Karen Cochrane Carlson
Assistant Examiner—Holly Schnizer
(74) Attorney, Agent, or Firm—Finnegan, Henderson, Farabow, Garrett and Dunner, L.L.P.

(57) ABSTRACT

The present invention relates to novel compounds and pharmaceutical composition, their preparation, and their use, having a antithrombotic effect through reversible inhibition of activated blood coagulation factor VIIa "FVIIa".

25 Claims, No Drawings

FACTOR VIIA INHIBITORS

Under the provisions of Section 119 of 35 U.S.C., Applicants hereby claim the benefit of the filing date of European Patent Application Number 98117506.0, filed Sep. 15, 1998, which Application is hereby incorporated by reference.

FIELD OF THE INVENTION

The present invention relates to novel compounds and compositions, their preparation and their use, having a strong antithrombotic effect through reversible inhibition of activated blood coagulation factor VIIa "FVIIa".

BACKGROUND OF THE INVENTION

Thrombus formation is normally the result of tissue injury which initiates the coagulation cascade and has the effect of slowing or preventing blood flow in wound healing. Other factors which are not directly related to tissue injury like atherosclerosis and inflammation may also initiate the coagulation cascade and may lead to pathological consequences.

Blood coagulation is a complex process involving a progressively amplified series of enzyme activation reactions in which plasma zymogens are sequentially activated by limited proteolysis. Mechanistically, the blood coagulation cascade has been divided into intrinsic and extrinsic pathways, which converge at the activation of factor X; subsequent generation of the thrombin proceeds through a single common pathway (see Scheme 1).

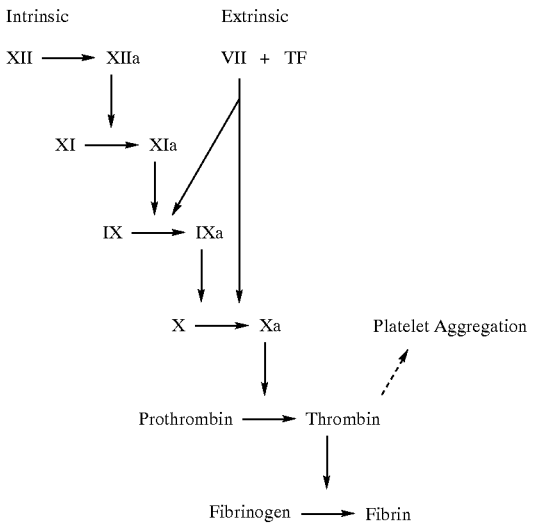

Scheme 1: Blood coagulation cascade

Present evidence suggests that the intrinsic pathway plays an important role in the maintenance and growth of fibrin formation, while the extrinsic pathway is critical in the initiation phase of blood coagulation (H. Cole, Aust. J. Med. Chem. 16 (1995) 87; G. J. Broze, Blood Coagulation and Fibrinolysis, Vol. 6, Suppl.1 (1995) S7–S13). It is generally accepted that blood coagulation is physically initiated upon formation of a tissue factor(TF)/factor VIIa complex. Once formed, this complex rapidly initiates coagulation by activating factors IX and X. The newly generated activated factor X, i.e., factor Xa, then forms a one-to-one complex with factor Va and phospholipids to form a prothrombinase complex, which is responsible for converting soluble fibrinogen to insoluble fibrin via the activation of thrombin from its precursor prothrombin. As time progresses, the activity of the factor VIIa/tissue factor complex (extrinsic pathway) is suppressed by a Kunitz-type protease inhibitor protein, TFPI, which, when complexed to factor Xa, can directly inhibit the proteolytic activity of factor VIIa/tissue factor. In order to maintain the coagulation process in the presence of an inhibited extrinsic system, additional factor Xa is produced via the thrombin-mediated activity of the intrinsic pathway. Thus, thrombin plays a dual autocatalytic role, mediating its own production and the conversion of fibrinogen to fibrin.

The autocatalytic nature of thrombin generation is an important safeguard against uncontrolled bleeding and it ensures that, once a given threshold level of prothrombinase is present, blood coagulation will proceed to completion. The ability to form blood clots is vital to survival. In certain disease states, however, the formation of blood clots within the circulatory system is itself a source of morbidity. It is nevertheless not desirable in such disease states to completely inhibit the clotting system because life threatening hemorrhage would ensue. Thus, it is most desirable to develop agents that inhibit coagulation by inhibition of factor VIIa without directly inhibiting thrombin.

In many clinical applications, there is a great need for the prevention of intravascular blood clots or for some anticoagulant treatment. The currently available drugs are not satisfactory in many specific clinical applications. For example, nearly 50% of patients who have undergone a total hip replacement develop deep vein thrombosis "DVT". The currently approved therapies are fixed dose low molecular weight heparin "LMWH" and variable dose heparin. Even with these drug regimes 10% to 20% of patients develop DVT and 5% to 10% develop bleeding complications.

Another clinical situation for which better anticoagulants are needed concerns subjects undergoing transluminal coronary angioplasty and subjects at risk for myocardial infarction or suffering from crescendo angina. The present, conventionally accepted therapy, which consists of administering heparin and aspirin, is associated with a 6% to 8% abrupt vessel closure rate within 24 hours of the procedure. The rate of bleeding complications requiring transfusion therapy due to the use of heparin also is approximately 7%. Moreover, even though delayed closures are significant, administration of heparin after termination of the procedures is of little value and can be detrimental.

The most widely used blood-clotting inhibitors are heparin and the related sulfated polysaccharides, LMWH, and heparin sulfate. These molecules exert their anti-clotting effects by promoting the binding of a natural regulator of the clotting process, anti-thrombin III, to thrombin and to factor Xa. The inhibitory activity of heparin primarily is directed toward thrombin, which is inactivated approximately 100 times faster than factor Xa. Hirudin and hirulog are two additional thrombin-specific anticoagulants presently in clinical trials. However, these anticoagulants, which inhibit thrombin, also are associated with bleeding complications. Preclinical studies in baboons and dogs have shown that targeting enzymes involved at earlier stages of the coagulation cascade, such as factor Xa or factor VIIa, prevents clot formation without producing the bleeding side effects observed with direct thrombin inhibitors. T. Yokoyama, A. B. Kelly, U. M. Marzec, S. R. Hanson, S. Kunitada, L. A. Harker, Circulation 92 (1995) 485–491; L. A Harker, S. R. Hanson, A. B. Kelly, Thromb. Hemostas. 74 (1995)

464–472; C. R. Benedict, J. Ryan, J. Todd, K. Kuwabara, P. Tyburg, Jr., J. Cartwright, D. Stern, Blood 81 (1993) 2059–2066.

Specific inhibition of the factor VIIa/TF catalytic complex using monoclonal antibody (International Patent Application No. WO92/06711) and a protein such as chloromethyl ketone inactivated FVIIa (International Patent Application No. WO96/12800 and WO97/47651) is an extremely effective means of controlling thrombus formation caused by acute arterial injury or the thrombotic complications related to bacterial septicemia. There is also experimental evidence suggesting that inhibition of factor VIIa/TF activity inhibits restenosis following ballon angioplasty. L. A. Harker, S. R. Hanson, J. N. Wilcox, A. B. Kelly, Haemostasis 26 (1996) S1:76–82. Bleeding studies have been conducted in baboons and indicate that inhibition of the factor VIIa/TF complex has the widest safety window with respect to therapeutic effectiveness and bleeding risk of any anticoagulant approach tested including thrombin, platelet and factor Xa inhibition. L. A. Harker, S. R. Hanson, A. B. Kelly, Thromb. Hemostas. 74 (1995) 464–472.

A specific inhibitor of factor VIIa would have substantial practical value in the practice of medicine. In particular, a factor VIIa inhibitor would be effective under circumstances where the present drugs of choice, heparin and related sulfated polysaccharides, are ineffective or only marginally effective. Thus, there exists a need for a low molecular weight, factor VIIa-specific blood clotting inhibitor that is effective, but does not cause unwanted side effects. The present invention satisfies this need by providing factor VIIa activity inhibiting derivatives of formula I and by providing related advantages as well.

The compounds of formula I are inhibitors of the blood clotting enzyme factor VIIa. The invention also relates to processes for the preparation of the compounds of formula I, to methods of inhibiting factor VIIa activity and of inhibiting blood clotting, to the use of the compounds of formula I in the treatment and prophylaxis of diseases which can be cured or prevented by the inhibition of factor VIIa activity such as thromboembolic diseases including thrombosis, restenosis, infarction, and angina, and the use of the compounds of formula I in the preparation of medicaments to be applied in such diseases. The invention further relates to compositions containing a compound of formula I in a mixture or otherwise in association with an inert carrier, in particular pharmaceutical compositions containing a compound of formula I together with pharmaceutically acceptable carrier substances or excipients and/or auxiliary substances or additives.

SUMMARY OF THE INVENTION

The present invention provides compounds that specifically inhibit factor VIIa activity. In particular, a subject of the present invention are compounds of the formula I:

  (I)

wherein:
R1 is
  R13,
  R12C(O), or
  1 to 3 amino acids having an N-terminus, the N-terminus of which is optionally substituted with a substituent chosen from R14C(O), R15S(O)$_2$, and an amino protecting group, wherein:
    R12 is chosen from alkyl, alkenyl, alkynyl, alkyloxy, alkylamino, alkenylamino, alkynylamino, alkenyloxy, alkynyloxy, aryl, heteroaryl, heterocycloalkyl, arylalkyl, heteroarylalkyl, heterocycloalkylalkyl, heteroalkyl, heteroalkenyl, and heteroalkynyl, which residues are all optionally substituted,
    R13 is chosen from an amino protecting group, hydrogen, alkyl, aryl, arylalkyl, heteroaryl, heteroarylalkyl, heterocycloalkyl, and heterocycloalkylalkyl, and
    R14 and R15 are independently chosen from alkyl, aryl, arylalkyl, heteroaryl, heteroarylalkyl, heterocycloalkyl and heterocycloalkylalkyl;
A is the group A1-A2-A3, wherein:
  A1 is NH,
  A2 is CHR93, wherein R93 is 4-amidinophenylmethyl,
  A3 is C(O);
B is the group B1-B2-B3, wherein:
  B1 is NR95, wherein R95 is chosen from hydrogen and alkyl,
  B2 is CHR97, wherein R97 is ethyl which is substituted in the 2-position by a substituent chosen from hydroxycarbonyl, alkyloxycarbonyl, and arylalkyloxycarbonyl,
  B3 is C(O);
D is the group D1-D2-D3, wherein:
  D1 is NH,
  D2 is CR81R82, wherein R81 and R82 are independently chosen from hydrogen and the unsubstituted or substituted residues alkyl, aryl, arylalkyl, heteroaryl, heteroarylalkyl, heterocycloalkyl, and heterocycloalkylalkyl, and
  D3 is C(O);
E$_n$ is (E1-E2-E3)$_n$, wherein:
  n is zero, one, two, or three,
  E1 is NR70, wherein R70 is chosen from hydrogen, alkyl, aryl, arylalkyl, heteroaryl, heteroarylalkyl, heterocycloalkyl, and heterocycloalkylalkyl,
  E2 is CR71R72, wherein R71 and R72 are independently chosen from hydrogen and the unsubstituted or substituted residues alkyl, aryl, arylalkyl, heteroaryl, heteroarylalkyl, heterocycloalkyl, and heterocycloalkylalkyl, and
  E3 is C(O); and
R2 is chosen from NR21R22, OR23 and R24, wherein R21, R22, R23, and R24 are independently chosen from hydrogen and the unsubstituted or substituted residues alkyl, aryl, arylalkyl, heteroaryl, heteroarylalkyl, heterocycloalkyl, and heterocycloalkylalkyl;

wherein alkyl and heteroalkyl contain 1 to 13 carbon atoms, and in a heteroalkyl residue one or more carbon atoms are replaced with heteroatoms chosen from N, O, and S; alkenyl, alkynyl, heteroalkenyl, and heteroalkynyl contain 2 to 13 carbon atoms, and in a heteroalkenyl and heteroalkynyl residue one or more carbon atoms are replaced with heteroatoms chosen from N, O, and S; aryl and heteroaryl contain 5 to 13 ring carbon atoms and in a heteroaryl residue one or more carbon atoms are replaced with heteroatoms chosen from N, O, and S; heterocycloalkyl contains 3 to 8 ring carbon atoms of which one to three carbon atoms are replaced with heteroatoms chosen from N, O, and S.

The present invention further includes the above compounds in any of their stereoisomeric forms and mixtures thereof in any ratio, and the pharmaceutically acceptable salts thereof.

DETAILED DESCRIPTION OF THE INVENTION

The present invention provides compounds, including peptides, of the formula I:

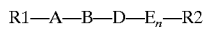 (I)

wherein R1, R2, A, B, D, E, and n are defined as above. Such compounds inhibit factor VIIa activity, but do not substantially inhibit the activity of other proteases involved in the blood coagulation pathway. The compounds of formula I contain structural units (for example in the groups A, B, D, or E, or in the group R1 in the case where R1 represents one, two, or three amino acids) which are amino acids, derivatives thereof, amino acid analogs, or mimetic structures, and which in peptide fashion are linked to adjacent groups via amide bonds (C(O)—N formed between (a) a carboxy group of one such amino acid, derivative thereof, amino acid analog, or mimetic structure and (b) an amino group of another amino acid, derivative thereof, amino acid analog, or mimetic structure.) As common in peptide chemistry, a divalent residue of an amino acid or of a group like A, B, D, or E as present in formula I is obtained from the respective amino acid by formally removing a hydrogen atom from an amino group and a hydroxy group from a carboxy group.

As used herein, the term "amino acid" is used in its broadest sense to include the twenty naturally occurring amino acids, which are translated from the genetic code and comprise the building blocks of proteins, including, unless specifically stated otherwise, L-amino acids and D-amino acids, as well as chemically modified amino acids such as amino acid analogs, naturally-occurring amino acids that are not usually incorporated into proteins such as norleucine, and chemically synthesized compounds having properties known in the art to be characteristic of an amino acid. For example, analogs or mimetics of phenylalanine or proline, which allow the same conformational restriction of the peptide compounds as natural Phe or Pro, are included within the definition of "amino acids" and are known to those skilled in the art. Such analogs and mimetics are referred to herein as "functional equivalents" of an amino acid. Other examples of amino acids and amino acids analogs are listed by Roberts and Vellaccio. The Peptides: Analysis, Synthesis, Biology, eds. Gross and Meienhofer, vol. 5, p. 341, Academic Press, Inc., New York 1983, which is incorporated herein by reference. Abbreviations of amino acids, amino acid analogs and mimetic structures as well as other abbreviations used in the application are listed in Table 1.

TABLE 1

Abbreviations used in the application

| Compound/Residue | Abbreviation |
|---|---|
| Acetic acid | AcOH |
| Acetylaminomethyl | Acm |
| Alanine | Ala |
| Allyloxycarbonyl | Alloc |
| p-Amidinophenylalanine | pAph |
| 2-Aminobutyric acid | 2-Abu |
| Arginine | Arg |
| Asparagine | Asn |
| Aspartic acid | Asp |
| Benzyl | Bzl |

TABLE 1-continued

Abbreviations used in the application

| Compound/Residue | Abbreviation |
|---|---|
| t-Butyloxycarbonyl | Boc |
| t-Butyl | tBu |
| Cyclohexylglycine | Chg |
| Cyclohexyl | Chx |
| Cyclohexylalanine | Cha |
| Cysteine | Cys |
| 2,4-Diaminobutyric acid | Dab |
| 2,3-Diaminopropionic acid | Dap |
| Dichloromethane | DCM |
| Diisopropylcarbodiimide | DIC |
| Diisopropyethylamine | DIEA |
| N,N-Dimethylformamide | DMF |
| Dimethylsulfoxide | DMSO |
| 9-Fluorenylmethyloxycarbonyl | Fmoc |
| Glutamic acid | Glu |
| Glutamine | Gln |
| Glycine | Gly |
| Histidine | His |
| N-Hydroxybenzotriazole | HOBt |
| 4-Hydroxymethylphenoxy-acetic acid | HMPA |
| Isoleucine | Ile |
| Leucine | Leu |
| Lysine | Lys |
| Methyl | Me |
| N-Methylimidazole | NMI |
| N-Methylmorpholine | NMM |
| 2,2,5,7,8-Pentamethyl-chroman-6-sulfonyl | Pmc |
| Ornithine | Orn |
| Phenyl | Ph |
| Phenylalanine | Phe |
| Phenylglycine | Phg |
| Proline | Pro |
| Serine | Ser |
| Tetrahydrofuran | THF |
| Tetramethylfluoroformamidino-hexafluorophosphate | TFFH |
| Threonine | Thr |
| Trifluoroacetic acid | TFA |
| Trityl | Trt |
| Tryptophan | Trp |
| Valine | Val |

Unless specified otherwise, amino acids abbreviated as specified above have L configuration. Amino acids of D configuration are denoted by D-prefix using three-letter code (for example D-Ala, D-Cys, D-Asp, D-Trp, D-pAph). Abbreviations such as, for example, Phe(4-CN) and Phe[4-C(—S—CH$_2$—CH$_2$—S—)—Ph] denote the residue of the amino acid phenylalanine which in the 4-position of the phenyl group carries a cyano substituent or a 2-phenyl-1,3-dithiolan-2-yl substituent, respectively. An abbreviation such as, for example, Dap[—C(=NH)—NH$_2$] denotes the residue of the amino acid 2,3-diaminopropionic acid in which the amino group in the side chain, i.e., the amino group in the 3-position, is substituted with an amidino group —C(=NH)—NH$_2$ (carbamimidoyl group) whereby a guanidino group —NH—C(=NH)—NH$_2$ attached to the 3-position of the propionic acid unit results. Abbreviations such as, for example, Orn[—C(=NH)—NH$_2$] or Cys(Me) denote the residue of the amino acid ornithine in which the amino group in the side chain carries an amidino group, or the residue of the amino acid cysteine in which the mercapto group carries a methyl group, respectively.

The terms TOTU, HATU, and BOP mean O-[cyan (ethoxycarbonyl)methylenamino]-1,1,3,3etramethyluronium tetrafluoroborate, O-(7-azabenzotriazol-1-yl)-1,1,3,3-tetramethyluronium hexafluorophosphate, and 1-benzotriazolyloxy-tris-(dimethylamino)-phosphonium hexafluorophosphate, respectively.

As used herein, the term "specific" when used in reference to the inhibition of factor VIIa activity means that a compound of the formula I can inhibit factor VIIa activity without substantially inhibiting the activity of other specified proteases, including plasmin and thrombin (using the same concentration of the inhibitor). Such proteases are involved in the blood coagulation and fibrinolysis cascade.

As used herein, the term "substituent" refers to any of various chemical groups that is substituted onto the peptide backbone or side chain of a peptide, peptide analogue, mimetic or organic compound disclosed herein. A substituent can include any of a variety of different moieties known to those skilled in the art. See, e.g., Giannis and Kolter, Angew. Chem. Int. Ed. Engl. 32 (1993)1244–1267, which is incorporated herein by reference.

As used herein, the term "alkyl" is used in the broadest sense to mean saturated or unsaturated, linear, branched or cyclic chains of 1 to about 13 carbon atoms where, of course, an unsaturated alkyl group contains at least 2 carbon atoms and a cyclic alkyl group at least 3 carbon atoms. An unsaturated group can contain one or more double bonds and/or triple bonds. Thus, the term "alkyl" includes, for example, methyl, ethyl, n-propyl, isopropyl, n-butyl, isobutyl, sec-butyl, tert-butyl, 1-methylbutyl, 2,2-dimethylbutyl, 2-methylpentyl, 2,2-dimethylpropyl, n-pentyl and n-hexyl groups, alkylene groups, cyclic chains of carbon atoms (such as cyclopropyl, cyclobutyl, cyclopentyl, cyclohexyl and cycloheptyl groups), as well as combinations of linear or branched chains and cyclic chains of carbon atoms (such as a methylcyclohexyl-, cyclohexylmethyl-, 1-cyclohexylethyl-, 2-cyclohexylethyl-, cyclopentylmethyl-, 1-cyclopentylethyl-, 2-cyclopentylethyl-, cyclopropylmethyl-, 1-cyclopropylethyl-, 2-cyclopropylethyl, or cyclopropylmethylene group). Thus, alkyl also comprises cyclic alkyl groups which carry one or more alkyl substituents. Further examples of alkyl are the below-mentioned specific unsaturated groups. In addition, it should be recognized that an alkyl as defined herein can be substituted with one or more identical or different substituents, for example one, two, three, or four substituents, which can be present in any desired suitable position.

In many cases, the term "alkyl" means saturated, linear or branched chains of from 1 to 6 carbon atoms, unsaturated linear or branched chains of from 2 to 6 carbon atoms, or cyclic alkyl groups of from 3 to 8 carbon atoms, in particular of from 3 to 6 or of from 4 to 6 ring carbon atoms. With respect to unsaturated alkyl chains, $(C_{2-C6})$-alkenyl and $(C_{2-C6})$-alkynyl are often utilyzed. Examples of unsaturated alkyl groups are alkenyl and alkynyl groups such as vinyl, prop-1-enyl, prop-2-enyl (=allyl), but-2-enyl, buten-3-yl, 3-methylbut-2-enyl, ethinyl, prop-2-ynyl, but-2-ynyl, and the like.

Similarly, the term "acyl" is used in its broadest sense to mean saturated or unsaturated, linear, branched, or cyclic chains of about 1 to 13 carbon atoms or aryl groups having 5 to 13 ring carbon atoms which are attached to a carbonyl moiety —C(O)— and are bonded via said carbonyl group. An acyl group can be considered as derived from the respective compound containing a carboxyl group C(O)—OH by formal removal of the hydroxy group. Thus, the term "acyl" encompasses, for example, groups such as formyl, acetyl, benzoyl, and the like. A group of acyl groups encompasses the hereinbefore mentioned saturated or unsaturated, linear, branched or cyclic chains having the preferred range of carbon atoms, which in addition contain a carbonyl group via which they are bonded.

The term "aryl" refers to aromatic groups containing about 5 to 13 ring carbon atoms and at least one "ring" group having a conjugated pi electron system. Often, the term "aryl" refers to aromatic groups having 6 to 10 ring carbon atoms. Examples of aryl include, for example, phenyl, naphthyl (such as 1-naphthyl and 2-naphthyl), fluorenyl, biphenylyl groups, and analogues and derivatives thereof, all of which are optionally substituted with one or more, e.g, one, two, three, or four, identical or different substituents which can be present in any desired suitable position. For example, a monosubstituted phenyl group is optionally substituted in the 2-, 3-, or 4-position, and a disubstituted phenyl group in the 2,3-, 2,4-, 2,5-, 2,6-, 3,4-, or 3,5-positions.

The term "arylalkyl" refers to an alkyl as defined above substituted with one or more (e.g, one or two) identical or different aryl groups. Suitable arylalkyl groups include benzyl, phenylethyl (such as 1-phenylethyl and 2-phenylethyl), diphenylmethyl, diphenylethyl (such as 1,2-diphenylethyl and 2,2-diphenylethyl), phenylpropyl (such as 1-phenylpropyl, 2-phenylpropyl and 3-phenylpropyl), diphenylpropyl (such as 2,3-diphenylpropyl and 3,3-diphenylpropyl), naphthylmethyl, naphthylethyl (such as 1-naphthylethyl and 2-naphthylethyl), naphthylpropyl (such as 1-naphthylpropyl, 2-naphthylpropyl and 3-naphthylpropyl), 1,2,3,4-tetrahydro-1-naphthyl, 1,2,3,4-tetrahydro-2-naphthyl, and the like, all of which are optionally substituted.

The terms "heteroalkyl", "heteroalkenyl", "heteroalkynyl", "heteroarylalkyl", and "heteroaryl" as used herein refer to an alkyl, arylalkyl, and aryl group, respectively, wherein one or more carbon atoms, for example one, two, three, or more carbon atoms, are replaced with identical or different heteroatoms (such as N, O, or S). In addition, the term "heterocycloalkyl" is used in reference to a cyclic alkyl group in which one or more ring carbon atoms are replaced with heteroatoms. The term "heterocycloalkyl" means a cyclic alkyl group having 3 to 8 ring carbon atoms, of which one, two, three, or more are replaced with identical or different hetero atoms such a N, O, or S. All of these groups can be bonded via any desired suitable position including suitable ring nitrogen atoms in the case of nitrogen heterocycles. Suitable heteroaryl groups, heteroarylalkyl groups, heteroalkyl groups, and heterocycloalkyl groups include, for example, 2-pyridyl, 3-pyridyl, 4-pyridyl, 2-thienyl, 3-thienyl, indolyl, imidazolyl, furyl, piperonyl, 2-pyridylmethyl, 3-pyridylmethyl, 4-pyridylmethyl, 1-(2-pyridyl)ethyl, 1-(3-pyridyl)ethyl, 1-(4-pyridyl)ethyl, 2-(2-pyridyl)ethyl, 2-(3-pyridyl)ethyl, 2-(4-pyridyl)ethyl, picolyl, pyrrolidinyl, piperidinyl, tetrahydrofuryl, tetrahydrofuran-2-ylmethyl, morpholinyl, 4-morpholinyl, 2-(4-morpholinyl)ethyl, piperazinyl, 2-(4-methylpiperazin-1-yl)ethyl, and the like, all of which are optionally substituted with one or more (e.g., one, two, three, or four) identical or different substituents.

The compounds of the invention are optionally modified at the N-terminus and/or the C-terminus by reaction with suitable reagents or by introduction (or by the presence of an amino-protecting group or carboxy-protecting group, respectively. The N-terminus of a peptide or peptide analog can be chemically modified such that the N-terminus amino group is substituted, for example, by an acyl group (e.g., acetyl, cyclopentylcarbonyl, isoquinolylcarbonyl, furoyl, tosyl, benzoyl, pyrazinecarbonyl or other such groups), by reaction with an isocyanate, chloroformate, or alkylating agent, or by introducing other such groups, all of which can be substituted by a substituent as described above. It should be recognized that the term "amino group" is used broadly herein to refer to any free amino group, including a primary, secondary, or tertiary amino group, present in a peptide. In comparison, the term "N-terminus" refers to the α-amino group of the first amino acid present in a peptide written in the conventional manner.

The N-terminus of a compound of the invention can be protected by linking thereto an amino-protecting group. The term "amino-protecting group" is used broadly herein to refer to a chemical group that can react with a free amino group, including, for example, the α-amino group present at the N-terminus of a compound of the invention. By virtue of reacting therewith, an amino-protecting group protects the otherwise reactive amino group against undesirable reactions as can occur, for example, during a synthetic procedure or due to exopeptidase activity on a final compound. Modification of an amino group also can provide additional advantages, including, for example, increasing the solubility or the activity of the compound. Various amino-protecting groups are disclosed herein or otherwise known in the art and include, for example, acyl groups (such as an acetyl, tert-butyloxycarbonyl, allyloxycarbonyl, benzyloxycarbonyl group or benzoyl groups), as well as an aminoacyl residue, which itself can be modified by an amino-protecting group. Other amino-protecting groups are described, for example, in The Peptides, eds. Gross and Meienhofer, vol. 3 (Academic Press, Inc., New York, 1981); and by Greene and Wuts, in Protective Groups in Organic Synthesis, 2d ed., pages 309–405 (John Wiley & Sons, New York, 1991), each of which is incorporated herein by reference. The product of any such modification of the N-terminus amino group of a peptide or peptide analog of the invention is referred to herein as an "N-terminal derivative."

Similarly, a carboxy group such as the carboxy group present at the C-terminus of a peptide can be chemically modified using a carboxy-protecting group. The terms "carboxy group" and "C-terminus" are used in a manner consistent with the terms "amino group" and "N-terminus" as defined above. A carboxy group such as that present at the C-terminus of a peptide can be modified by reduction of the C-terminus carboxy group to an alcohol or aldehyde or by formation of an oral ester or by substitution of the carboxy group with a substituent such as a thiazolyl, cyclohexyl or other group. Oral esters are well known in the art and include, for example, alkyloxymethyl groups (such as methoxymethyl, ethoxymethyl, isopropoxymethyl, and the like); the 1-(($C_1$–$C_4$)-alkyloxy)ethyl groups (such as methoxyethyl, ethoxyethyl, propoxyethyl, isopropoxyethyl and the like); the 2-oxo-1,3-dioxolen4-ylmethyl groups (such as 5-methyl-2-oxo-1,3-dioxolen4-ylmethyl, 5-phenyl-2-oxo-1,3-dioxolen4-ylmethyl, and the like); the (($C_1$–$C_3$)-alkylthio)methyl groups (such as methylthiomethyl, ethylthiomethyl, isopropylthiomethyl, and the like); the acyloxymethyl groups (such as pivaloyloxymethyl, acetoxymethyl, and the like); the ethoxycarbonylmethyl group; the 1-acyloxy-1-substituted methyl groups (such as 1-acetoxyethyl; the 3-phthalidyl, or 5,6-dimethylphthalidyl groups); the 1-((($C_1$–$C_4$)-alkyloxy)carbonyloxy)ethyl groups (such as the 1-(ethoxycarbonyloxy)ethyl group); and the 1-((($C_1$–$C_4$)-alkylamino)carbonyloxy)ethyl group (such as the 1-(methylaminocarbonyloxy)ethyl group).

A compound of the invention can be modified by linking thereto a carboxy-protecting group. Carboxy-protecting groups are well known in the art and, by virtue of being bound to a peptide, protect a carboxy group against undesirable reactions. See, e.g., Greene and Wuts, supra, pages 224–276 (1991), which is incorporated herein by reference.

The skilled artisan would recognize that such modifications as described above, which can be effected upon the N-terminus amino group or C-terminus carboxy group of a peptide, similarly can be effected upon any reactive amino group or carboxy group present, for example, on a side chain of an amino acid or amino acid analog in a compound of the invention. Methods for performing such modifications are disclosed herein or otherwise known in the art.

The choice of including an L- or a D-amino acid in a compound of the present invention can depend, in part, on the desired characteristics of the peptide. For example, the incorporation of one or more D-amino acids can confer increased stability on the compound in vitro or in vivo. The incorporation of one or more D-amino acids also can increase or decrease the pharmacological activity of the compound. In some cases, it can be desirable to allow the compound to remain active for only a short period of time. In such cases, the incorporation of one or more L-amino acids in the compound can allow endogenous peptidases in an individual to digest the compound in vivo, thereby limiting the individual's exposure to the active compound. The skilled artisan can determine the desirable characteristics required of a compound of the invention by taking into consideration, for example, the age and general health of an individual.

In general, the present invention relates to the compounds of the formula I in all their stereoisomeric forms and mixtures of two or more stereosiomers in all ratios, including, for example, pure enantiomers, pure diastereomers, mixtures of two enantiomers in all ratios including racemates, mixtures of diastereomers, cis isomers, trans isomers, E isomers, or Z isomers. The invention also relates to the compounds of the formula I in all their tautomeric forms. Further, the invention relates to prodrugs of the compounds of the formula I, for example esters, amides, aldehydes or alcohols obtainable from carboxy groups as already mentioned, or acyl derivatives like ($C_1$–$C_6$)-alkylcarbonyl, ($C_1$–$C_6$)-alkyloxycarbonyl or aryl-($C_1$–$C_4$)-alkyloxycarbonyl derivatives obtainable from acylatable groups including amino groups, imino groups, guanidino groups and amidino groups. The invention also relates to active metabolites of the compounds of the formula I.

In one embodiment of the compounds of the formula I, the group R1 preferably is R12C(O). A specific series of denotations of R12 is formed by the groups alkyl, alkenyl, alkynyl, alkyloxy, alkylamino, alkenylamino, alkynylamino, alkenyloxy, alkynyloxy, aryl, heteroaryl, heterocycloalkyl, heteroarylalkyl, heterocycloalkylalkyl, heteroalkyl, heteroalkenyl, and heteroalkynyl, which residues can all be unsubstituted or substituted. R12 preferably is alkyl, alkenyl, alkynyl, alkyloxy, alkenyloxy, alkynyloxy, alkylamino, alkenylamino, alkynylamino, aryl, heteroaryl, arylalkyl, or heteroarylalkyl, and more preferably R12 is alkenyloxy, alkenylamino or aryl, which residues can all be unsubstituted or substituted. Particularly preferably R12 is alkenyloxy or alkenylamino like ($C_2$–$C_6$)-alkenyloxy or ($C_2$–$C_6$)-alkenylamino wherein each contains one double bond, for example allyloxy or allylamino. More preferably, R12 is ($C_2$–$C_6$)-alkenyloxy. The residues representing R12 can be unsubstituted or substituted. In substituted residues R12 the residues preferably are substituted with one or more identical or different substituents chosen from halogen (i.e, flourine, chlorine, bromine or iodine), trifluoromethyl, hydroxy, nitro, amino, cyano, carboxy, aminocarbonyl, alkylsulfonyl, aminosulfonyl, alkyloxy, alkylcarbonylamino, and mono- or dialkylamino. Similarly, the residues representing R13, R14, and R15 can be unsubstituted or substituted, for example by the substituents that can be present in R12, where R14 and R15 are independent of each other and can be identical or different. Particularly preferably, R1 is allyloxycarbonyl or allylaminocarbonyl.

The group A in the compounds of the formula I which is the divalent 4-amidinophenylalanine residue —NH—CH[—CH$_2$—C$_6$H$_4$—(4-C(=NH)—NH$_2$)]—C(O)—, preferably is an (L)-4-amidinophenylalanine residue (=(S)-4-amidinophenylalanine residue). The group B which is the divalent glutamic acid residue —NH—CH[—CH$_2$—CH$_2$—C(O)OH]—C(O)— or a pharmaceutically acceptable salt or ester thereof, preferably is an (L)-glutamic acid residue (=(S)-glutamic acid residue) or a pharmaceutically acceptable salt or ester thereof.

R95 preferably is hydrogen or (C$_1$–C$_4$)-alkyl, more preferably hydrogen or methyl, particularly preferably hydrogen.

Substituted residues R81 and R82 can independently carry one or more (for example one, two, three, four, etc.) identical or different residues which preferably are chosen from amino, aminocarbonyl, amidino, guanidino, aminoalkyl, hydroxy, mercapto, (which can all be substituted with a protecting group), and acetimido (—C(=NH)—CH$_3$), nitro, and cyano. With respect to nitro groups, in many embodiments of compounds of the formula I according to the invention, usually only up to two nitro groups are present. Suitable. protecting groups for the listed groups are known to one skilled in the art and can be found in the abovementioned references like Greene and Wuts, Protective Groups in Organic Synthesis, 2d ed., (John Wiley & Sons, New York, 1991), which is incorporated herein by reference. Examples of protecting groups are the abovementioned amino protecting groups like tert-butyloxycarbonyl, benzyloxycarbonyl, and allyloxycarbonyl (which can also be protective groups on amidino groups and guanidino groups), the nitro group (which can be used to protect a guanidino group), or groups like benzyl, methyl, trityl or acetylaminomethyl (which can be used to protect groups like hydroxy, mercapto, and others).

In certain embodiments, R81 and R82 are chosen from hydrogen, alkyl (such as (C$_1$–C$_6$)-alkyl), aryl (such as phenyl), arylalkyl (such as phenyl-(C$_1$–C$_2$)-alkyl) and heteroarylalkyl (such as heteroaryl-(C$_1$–C$_2$)-alkyl), which can all be unsubstituted or substituted and in which heteroaryl preferably is the residue of a monocyclic or bicyclic aromatic ring system containing one or two identical or different ring heteroatoms such as N, O, or S. In certain currently preferred embodiments of the present invention, R81 is hydrogen, and R82 is an unsubstituted or substituted residue as defined.

Particularly preferably, the group D represents a residue chosen from Arg, Dap, Dab, Orn, Lys, Dap[—C(=NH)—NH$_2$], Dab[—C(=NH)—NH$_2$], Lys[—C(=NH)—NH$_2$], Lys[—C(=NH)—CH$_3$], Orn[—C(=NH)—CH$_3$], Dab[—C(=NH)—CH$_3$], Dap[—C(=NH)—CH$_3$], Dab(Alloc), Asn, Gln, Met, Ser, Thr, Ser(Bzl), Thr(Bzl), Cys(Me), Cys(Bzl), Cys(Acm), Arg(NO$_2$), His, Trp, Phg, Gly, Ala, Val, Ile, Leu, Phe, Phe(4-NO$_2$), Phe(4-NH—C(=NH)—NH$_2$), 2-Abu, Ala(3-CN), Ala[3-C(=NH)—NH$_2$], 2-Abu(4-CN), and 2-Abu[4-C(=NH)—NH$_2$]. A subgroup of residues from which the particularly preferred residues D are chosen includes Arg, Dap, Dab, Orn, Lys, Dap[—C(=NH)—NH$_2$], Dab[~C(=NH)—NH$_2$], Lys[—C(=NH)—NH$_2$], Asn, Ser, Thr, Ser(Bzl), Arg(NO$_2$), Trp, Phg, Ala, Val, Ile, Leu, Phe, 2-Abu, Ala(3-CN), Ala(3-C(=NH)—NH$_2$), 2-Abu(4-CN) and 2-Abu(4-C(=NH)—NH$_2$).

The number n is preferably zero, one or two, more preferably zero or one. If n is zero the group R2 is directly bonded to the carbonyl group representing D3. If n is different from zero, the group R2 is bonded to the carbonyl group representing the terminal group E3. If n is two or three, the groups E can all be identical or different.

Substituted residues R71 and R72 can independently carry one or more (e.g., one, two, three, or four) identical or different residues which preferably are chosen from alkyl, alkyloxy, halogen, trifluoromethyl, nitro, cyano, alkylsulfonyl, alkylcarbonyl, phenylcarbonyl, and 2-phenyl-1,3-dithiolan-2-yl, which can be further substituted, for example by substituents including the foregoing. A subgroup of substituents which can be present in R71 and R72 is formed by the series comprising alkyl, alkyloxy, halogen, trifluoromethyl, nitro, cyano, alkylsulfonyl and alkylcarbonyl, which can be further substituted. Ofttimes, R71 is hydrogen and R72 is an unsubstituted or substituted residue as defined. R72 may be alkyl, in particular (C$_3$–C$_8$)-alkyl, including cyclic alkyl like cycloalkylalkyl (such as cycloalkyl-(C$_1$–C$_2$)-alkyl), or aryl (such as phenyl), or arylalkyl (such as phenyl-(C$_1$–C$_2$)-alkyl), or heteroarylalkyl (such as heteroaryl-(C$_1$–C$_2$)-alkyl, where all these residues can be unsubstituted or substituted and where heteroaryl preferably is a monocylic 5-membered or 6-membered aromatic ring containing one or two identical or different ring heteroatoms such as N, O, and S. The group or the groups E, in particular in the case where the number n is one, may be chosen from Phe (which is unsubstituted or substituted in the phenyl group), Cha, and Chg. In certain currently preferable embodiments, E is chosen from Cha, Chg, and Phe[4-C(—S—CH$_2$—CH$_2$—S—)—Ph]. The group R70 present in the group E is preferably hydrogen, alkyl (such as in particular (C$_1$–C$_4$)-alkyl including methyl), or arylalkyl (such as in particular phenyl-(C$_1$–C$_4$)-alkyl including benzyl and 2-phenylethyl which can be unsubstituted or substituted in the phenyl group). Particularly preferably, R70 is hydrogen.

Substituted residues R21, R22, R23, and R24 can independently carry one or more (e.g., one, two, three, four, or more) identical or different residues which may be chosen from halogen (such as F, Cl, or Br), hydroxy, trifluoromethyl, nitro, cyano, dialkylamino, alkyloxy (such as methyloxy), alkylenedioxy, alkylsulfonyl, aminosulfonyl, and oxo (=O), which can be further substituted, for example, by substituents including the foregoing. Examples of alkylenedioxy are methylenedioxy (O—CH$_2$—O) or 1,2-ethylenedioxy. Examples of dialkylamino are dimethylamino, diethylamino, or dibutylamino; examples of alkylsulfonyl are methylsulfonyl, ethylsulfonyl or butylsulfonyl.

R2 preferably is NR21R22 wherein R21 and R22 are as defined. R21 preferably is hydrogen, (C$_1$–C$_4$)-alkyl, or phenyl-(C$_1$–C$_4$)-alkyl which is unsubstituted or substituted in the phenyl group. Particularly preferably, R21 is hydrogen, i.e. NR21R22 is NHR22, and thus particularly preferably R2 is NHR22.

R22 preferably is a residue chosen from hydrogen, alkyl (such as (C$_1$–C$_{12}$)-alkyl including cyclic alkyl like cycloalkylalkyl (in particular cycloalkyl-(C$_1$–C$_4$)-alkyl)), aryl (such as (C$_6$–C$_{13}$)-aryl), arylalkyl (such as (C$_1$–C$_4$)-alkyl substituted with one or two (C$_6$–C$_{12}$)-aryl residues), heteroarylalkyl (such as (C$_1$–C$_4$)-alkyl substituted with a monocyclic or bicyclic heteroaryl residue containing one or two identical or different heteroatoms such as N, O, or S) and heterocycloalkylalkyl (such as (C$_1$–C$_4$)-alkyl substituted with a monocyclic 4-, 5-, 6- or 7-membered heterocycloalkyl group containing one or two identical or different heteroatoms such as N, O, or S), which residues can all be unsubstituted or substituted as indicated before. For example, the residue R22 may be substituted with substituents chosen from halogen, hydroxy, alkyloxy, alkylenedioxy, nitro, cyano, dialkylamino, alkylsulfonyl, aminosulfonyl and trifluoromethyl, which can be further substituted, for example, by substituents including the foregoing.

Particularly preferably, R22 is a residue chosen from hydrogen, benzyl, naphthylmethyl, pyridylmethyl, phenylethyl, naphthylethyl, pyridylethyl, phenylpropyl, naphthylpropyl, pyridylpropyl, fluorenyl, diphenylmethyl, diphenylethyl and diphenylpropyl, which residues are unsubstituted or substituted with one or more (e.g., one, two, three, or four) identical or different substituents,which may be chosen from F, Cl, Br, hydroxy, methoxy, methylenedioxy, nitro, cyano, dialkylamino, alkylsulfonyl, aminosulfonyl, and trifluoromethyl, which can be further substituted. A series of currently preferred compounds of the formula I is formed by compounds in which simultaneously the number n is different from zero, R2 is NHR22 and R22 is hydrogen. Another series of particularly preferred compounds is formed by compounds in which simultaneously n is zero, R2 is NHR22 and R22 is different from hydrogen, where in this series of compounds a preferred denotation of the group D is Asn.

Preferred compounds of the formula I are those compounds in which one or more of the groups or residues have preferred denotations, all combinations of preferred denotations being a subject of the present invention.

A group of currently preferred compounds of the invention is formed by compounds of the formula I wherein:

R1 is R12 C(O) wherein R12 is as defined;
A is as defined;
B is as defined, and preferably B is NH—CHR97—C(O) wherein R97 is ethyl which is substituted in the 2-position by hydroxycarbonyl or a salt thereof or alkyloxycarbonyl like $(C_1-C_4)$-alkyloxycarbonyl;
D is NH—CHR82—C(O), wherein R82 is as defined;
$E_n$ is $(E1-E2-E3)_n$, wherein:
  n is zero, one or two,
  E1 is NH,
  E2 is CHR72, wherein the residues R72 which are independent of each other and are identical or different, are as defined,
  E3 is C(O); and
R2 is as defined, in any of their stereoisomeric forms or a mixture thereof in any ratio, and the pharmaceutically acceptable salts, amides, and esters thereof.

A group of particularly preferred compounds is formed by the compounds of the formula I wherein:

R1 is allyloxycarbonyl or allylaminocarbonyl;
A is the residue of (L)-4-amidinophenylalanine;
B is the residue of (L)-glutamic acid residue or a pharmaceutically acceptable salt or ester of (L)-glutamic acid;
D is a residue chosen from Arg, Dap, Dab, Orn, Lys, Dap[—C(=NH)—NH$_2$], Dab[—C(=NH)—NH$_2$], Lys[—C(=NH)—NH$_2$], Lys[—C(=NH)—CH$_3$], Orn [—C(=NH)—CH$_3$], Dab[—C(=NH)—CH$_3$], Dap [—C(=NH)—CH$_3$], Dab(Alloc), Asn, Gln, Met, Ser, Thr, Ser(Bzl), Thr(Bzl), Cys(Me), Cys(Bzl), Cys (Acm), Arg(NO$_2$), His, Trp, Phg, Gly, Ala, Val, Ile, Leu, Phe, Phe(4-NO$_2$), Phe(4-NH—C(=NH)—NH$_2$), 2-Abu, Ala(3-CN), Ala[3-C(=NH)—NH$_2$], 2-Abu(4-CN), and 2-Abu[4-C(=NH)—NH$_2$];
n is zero or one;
E is a residue chosen from Cha, Chg, and Phe[4-C(—S—CH$_2$—CH$_2$—S—)—Ph];
R2 is NHR22;
R22 is hydrogen or a residue chosen from benzyl, naphthylmethyl, pyridylmethyl, phenylethyl, naphthylethyl, pyridylethyl, phenylpropyl, naphthylpropyl, pyridylpropyl, fluorenyl, diphenylmethyl, diphenylethyl, and diphenylpropyl, which residues are unsubstituted or substituted with one or more identical or different substituents chosen from F, Cl, Br, hydroxy, methoxy, methylenedioxy, nitro, cyano, dialkylamino, alkylsulfonyl, aminosulfonyl, and trifluoromethyl; and, wherein the above compounds are present in any of their stereoisomeric forms or a mixture thereof in any ratio, and the pharmaceutically acceptable salts, amides and esters thereof.

Specific examples of the compounds of the invention include, for example, the compounds listed in Table 2 below and in the example section, and their pharmaceutically acceptable salts, amides, and esters.

The compounds of the formula I can be prepared, for example, according to the methods of solid phase chemistry by a process which comprises the steps of:

(a1) coupling a compound of the formula Fmoc-E$_n$—OH, wherein n is one, two, or three, to an acid sensitive linker attached to a resin or in general a solid support, cleaving off the protecting group Fmoc, coupling a compound of the formula Fmoc-D1—D2—C(O)OH to the free amino group obtained and again cleaving off the protecting group Fmoc, or for the preparation of a compound of the formula I in which n is zero, coupling a compound of the formula Fmoc-D1—D2—C(O)OH to an acid sensitive linker attached to a resin or in general a solid support, and cleaving off the protecting group Fmoc;

(a2) coupling a compound of the formula Fmoc-B1—B2—C(O)OH to the free amino group obtained in step a1) and cleaving off the protecting group Fmoc;

(a3) coupling a compound of the formula R1—A1—A2—C(O)OH to the free amino group obtained in step a2); and (a4) cleaving off the compound obtained according to steps a1) through a3) from the resin by means of trifluoroacetic acid.

The resin or the linker used in this process may be of a type such that the carboxy group in the compound which is coupled to the resin or the linker, respectively, is transformed into an amide group C(O)—NH$_2$, for example, a Knorr Linker or a Rink amide resin. The preparation of a compound in which the number n is two or three can also be carried by stepwise assembling the unit E$_n$ as follows: In step (a1) instead of a compound of the formula Fmoc-E$_n$—OH wherein n is two or three, a compound of the formula Fmoc-E$_n$—OH wherein n is one is first coupled to an acid sensitive linker attached to a resin, then the protecting group Fmoc is cleaved off, and a second compound of the formula Fmoc-E$_n$—OH wherein n is one is coupled to the free amino group that has been obtained. For the preparation of a compound in which n is three, the protecting group Fmoc then is cleaved off, and a third compound of the formula Fmoc-E$_n$—OH wherein n is one is coupled to the free amino group that has been obtained. Finally, the protecting group Fmoc is cleaved off and steps (a2) through (a4) are performed.

Another process for the preparation of the compounds of the formula I comprises the steps of:

(b1) coupling the side chain carboxylic acid of a compound of the formula Fmoc-B1—CHR97—C(O)OPG, wherein R97 is 2-hydroxycarbonylethyl and PG is a protecting group to an acid sensitive benzylalcohol type of linker attached to an amino functionalized resin;

(b2) cleaving off the protecting group PG;

(b3) coupling a compound of the formula $H_2N$—D2—D3—$E_n$—R2, wherein n is zero, one, two or three, to the free carboxylic acid obtained in step (b2);

(b4) cleaving off the protecting group Fmoc;

(b5) coupling a compound of the formula R1—A1—A2—C(O)OH to the free amino group obtained in step b4); and (b6) cleaving off the compound obtained according to steps (b1) through (b5) from the resin by means of trifluoroacetic acid.

In a process similar to the modification of the first process described above, the structural unit $H_2N$—D2—D3—$E_n$—R2 may be assembled stepwise on the resin. According to a further process, the compounds of the formula I can also be prepared by first coupling a carboxylic acid group which is present in a side chain in the group D2 of the group D, i.e. which is present in one of the groups R81 and R82, to a linker attached to a resin. Analogously to the above compound of the formula Fmoc-B1—CHR97—C(O)OPG, such a compound may for example have the formula Fmoc-NH—CR81R82—C(O)OPG wherein R82 is as defined with the proviso that it contains a group C(O)OH, and R81 is as defined. For example, R81 can be hydrogen and R82 can be hydroxycarbonylmethyl, and the compound of the formula Fmoc-NH—CR81R82—C(O)OPG can thus be a protected aspartic acid derivative. After deprotecting the group C(O) OPG, the carboryl group of which is the group D3 in formula I, the free carboxylic acid group obtained is coupled with a compound like $H_2N$—$E_n$—R2 or H—R2. Then, after deprotecting the protecting group Fmoc, the amino group obtained is coupled with a compound of the formula Fmoc-B1—B2—C(O)OH and, after deprotecting the amino group, the product is coupled with a compound of the formula R1—A1—A2—C(O)OH. Again the resin or the linker used may be of a type such that the carboxy group in the compound which is coupled to the resin or the linker, is transformed into an amide group C(O)—$NH_2$. For example, by using an amide resin, an aspartic acid unit attached to the resin can be converted into an asparagine unit in the final compound.

A compound of the invention can be chemically synthesized using, for example, an automated synthesizer (see Example I). Selective modification of a reactive group such as a group present on an amino acid side chain or an N-terminus or a C-terminus reactive group in a peptide can impart desirable characteristics such as increased solubility or enhanced inhibitory function to a compound of the invention. Where solid phase synthesis methods are employed, the chemical composition of a compound can be manipulated while the nascent peptide is attached to the resin or after the peptide has been cleaved from the resin to obtain, for example, an N-terminal derivative such as an N-terminus acylated, e.g. acetylated, compound. Similar modifications also can be made to a carboxy group of a compound, including a C-terminus carboxy group, which can be amidated.

The compounds can also be prepared by coupling of protected amino adds according to the methods of traditional medicinal chemistry, or solution phase organic chemistry, and deprotecting to the target molecule, by standard procedures known in the art. In general, suitable reactions for the synthesis of the compounds of the formula I by solid phase methods or solution phase methods as well as experimental details like suitable coupling agents (such as carbodiimides, TOTU, or HATU) solvents, and reaction temperatures, are well known to one skilled in the art and can also be found in standard references including the references mentioned herein, and are also exemplified below.

A synthesized compound can be purified using well known methods such as reverse phase-high performance liquid chromatography (RP-HPLC; see Example I) or other methods of separation based, for example, on the size, charge, or hydrophobicity of the compound. Similarly, well known methods such as amino acid sequence analysis or mass spectrometry "MS" can be used for characterizing the structure of a compound of the invention (see Example I).

Various compounds containing different arrangements of the substituents exhibit different levels of inhibitory activity for factor VIIa. For example, the choice of the substituents influences the binding affinity of the compounds. These compounds were synthesized according to the procedures described in the Examples. Testing the peptides for inhibitory activity was accomplished using the assay described in Example 22. Using such methods, one skilled in the art can synthesize a compound as disclosed herein, including a modification thereof, and determine the factor VIIa inhibitory activity of the compound. A composition of the present invention can be provided as a homogenous composition or as a mixture of compounds containing various combinations of substituents. The flexibility permitted by the choice of substituents permits a great deal of control over the biological and physico-chemical properties of the compounds and compositions of the invention.

The invention provides compounds that specifically inhibit factor VII activity. Such compounds preferably have a Ki≦500 nM, more preferably ≦50 nM, for factor VIIa activity and do not substantially inhibit the activity of other proteases involved in coagulation and fibrinolysis cascade relative to the inhibition of factor VIIa (using the same concentration of the inhibitor). Such other proteases include, for example, factor Xa, thrombin, and plasmin.

The following Table 2 shows the factor VIIa inhibitory activities (see Example 22 for the method of determining Ki) of selected compounds of the formula I which also exemplify the invention.

TABLE 2

Factor VIIa inhibitory activities of selected compounds of the formula I

| | Ki (μM) |
|---|---|
| Alloc—pAph—Glu—Arg—Cha—$NH_2$ | 0.046 |
| Allylaminocarbonyl—pAph—Glu—Arg—Cha—$NH_2$ | 0.042 |

TABLE 2-continued

Factor VIIa inhibitory activities of selected compounds of the formula I

| | $K_i$ ($\mu$M) |
|---|---|
| Alloc—pAph—Glu—Arg—Chg—NH$_2$ | 0.238 |
| Alloc—pAph—Glu—Dap[—C(=NH)—NH$_2$]—Cha—NH$_2$ | 0.012 |
| Alloc—pAph—Glu—Ala[3-C(=NH)—NH$_2$]—Cha—NH$_2$ | 0.03 |
| Alloc—pAph—Glu—Asn—Cha—NH$_2$ | 0.021 |
| Alloc—pAph—Glu—Dab—Cha—NH$_2$ | 0.055 |
| Alloc—pAph—Glu—Dap[—C(=NH)—NH$_2$]—NH$_2$ | 0.26 |
| Alloc—pAph—Glu—Gly—Cha—NH$_2$ | 0.12 |
| Alloc—pAph—Glu—Thr(Bzl)—NH—(CH$_2$)$_2$—CH(Ph)$_2$ | 0.17 |
| Alloc—pAph—Glu—Dab—NH—(CH$_2$)$_2$—Ph | 0.38 |
| Alloc—pAph—Glu—Asn—NH—CH$_2$—Chx | 0.15 |
| Alloc—pAph—Glu—Dap[—C(=NH)—CH$_3$]—Cha—NH$_2$ | 0.11 |
| Alloc—pAph—Glu—Dab[—C(=NH)—NH$_2$]—Cha—NH$_2$ | 0.012 |
| Alloc—pAph—Glu-2-Abu(4-CN)—Cha—NH$_2$ | 0.063 |
| Alloc—pAph—Glu—Ala(3-CN)—Cha—NH$_2$ | 0.12 |
| Alloc—pAph—Glu—Asn-1-naphthylmethylamide | 0.031 |
| Alloc—pAph—Glu—Asn-1-(1-naphthyl)ethylamide | 0.021 |
| Alloc—pAph—Glu—Asn-2-naphthylmethylamide | 0.027 |
| Alloc—pAph—Glu—Asn-3,4-dichlorobenzylamide | 0.026 |
| Alloc—pAph—Glu—Asn-2-(3-chlorophenyl)ethylamide | 0.023 |
| Alloc—pAph—Glu—Arg(NO$_2$)—Cha—NH$_2$ | 0.014 |
| Alloc—pAph—Glu—Cys(Bzl)—Cha—NH$_2$ | 0.026 |
| Alloc—pAph—Glu—Trp—Cha—NH$_2$ | 0.017 |
| Alloc—pAph—Glu—Phg—Cha—NH$_2$ | 0.017 |
| Alloc—pAph—Glu—Asn-9-fluorenylamide | 0.023 |
| Alloc—pAph—Glu—Asn-3,5-bistrifluoromethylbenzylamide | 0.033 |
| Alloc—pAph—Glu—Phe(4-guanidino)—Cha—NH$_2$ | 0.12 |
| Alloc—pAph—Glu—D—Phe(4-guanidino)—Cha—NH$_2$ | 11.3 |
| Alloc—pAph—Glu—Orn[—C(=NH)—CH$_3$]—Cha—NH$_2$ | 0.13 |
| Alloc—pAph—Glu—Dab[—C(=NH)—CH$_3$]—Cha—NH$_2$ | 0.19 |
| Alloc—pAph—Glu—Dap[—C(=NH)—NH$_2$]—Phe[4-C(—S—(CH$_2$)$_2$—S—)—Ph]—NH$_2$ | 0.015 |
| Alloc—pAph—Glu—Gln—NH$_2$ | 1.5 |
| Alloc—pAph—Glu—Orn—NH$_2$ | 6.2 |
| Alloc—pAph—Glu—Gly—Cha—NH$_2$ | 0.12 |
| Alloc—pAph—Glu—Cys(Acm)—Cha—NH$_2$ | 0.12 |
| Alloc—pAph—Glu—Cys(Me)—Cha—NH$_2$ | 0.20 |
| Alloc—pAph—Glu—Cys(Bzl)—Cha—NH$_2$ | 0.026 |
| Alloc—pAph—Glu—Thr(Bzl)—Cha—NH$_2$ | 0.019 |
| Alloc—pAph—Glu—Dab(Alloc)—Cha—NH$_2$ | 0.15 |
| Alloc—pAph—Glu—His—Cha—NH$_2$ | 0.14 |
| Alloc—pAph—Glu—Met—Cha—NH$_2$ | 0.11 |
| Alloc—pAph—Glu—Phe(4-NO$_2$)—Cha—NH$_2$ | 0.046 |
| Alloc—pAph—Glu—D—Lys[—C(=NH)—NH$_2$]—Cha—NH$_2$ | 22 |
| Alloc—pAph—Glu—D—Arg—Cha—NH$_2$ | 12 |
| Alloc—pAph—Glu—Asn-3,4-methylenedioxybenzylamide | 0.12 |
| Alloc—pAph—Glu—Asn-2-(4-morpholinyl)ethylamide | 0.41 |
| Alloc—pAph—Glu—Asn-2-(2-naphthyl)ethylamide | 0.052 |
| Alloc—pAph—Glu—Asn-2-(1-naphthyl)ethylamide | 0.022 |
| Alloc—pAph—Glu—Asn-2-tetrahydrofuranylmethylamide | 0.17 |
| Alloc—pAph—Glu—Asn-3-methylbutylamide | 0.11 |
| Alloc—pAph—Glu—Asn-2-(2-pyridyl)ethylamide | 0.071 |
| Alloc—pAph—Glu—Asn-1,2,3,4-tetrahydro-1-naphthylamide | 0.045 |
| Alloc—pAph—Glu—Asn-N,N-dibenzylamide | 0.41 |
| Alloc—pAph—Glu—Asn-N-methyl-N-(1-naphthylmethyl)amide | 1.7 |
| Alloc—pAph—Glu—Asn-2,2-diphenylethylamide | 0.049 |
| Alloc—pAph—Glu—Asn-2,4-difluorobenzylamide | 0.051 |
| Alloc—pAph—Glu—Asn-2-(4-sulfamoylphenyl)ethylamide | 0.35 |
| Alloc—pAph—Glu—Asn-4-dimethylaminobenzylamide | 0.11 |
| Alloc—pAph—Glu—Asn—(CH$_3$—)Cha—NH$_2$ | 0.062 |
| Alloc—pAph—Glu—Asn-3-phenylpropylamide | 0.026 |
| Alloc—pAph—Glu—Asn-3,3-diphenylpropylamide | 0.024 |
| Alloc—pAph—Glu—Asn-4-methoxybenzylamide | 0.083 |
| Alloc—pAph—Glu—Asn-3,4-dichlorobenzylamide | 0.026 |

The thrombin inhibitory activities of the above compounds can be expressed in Ki values which generally are considerably higher than the above indicated factor VIIa inhibitory activities, for example about 200 or about 500 or about 1000 times as high as the factor VIIa inhibitory activities. Also, the factor Xa inhibitory activities of the above compounds as determined can be expressed in Ki values which generally are considerably higher than the above indicated factor VIIa inhibitory activities, for example about 100 times as high as the factor VIIa inhibitory activities.

These results demonstrate that the compounds of the formula I are useful as inhibitors of factor VIIa, but do not substantially inhibit the activity of factor Xa or serine proteases such as thrombine, which are involved in the process of blood coagulation and fibrinolysis.

A compound of the invention can be used advantageously as an anticoagulant, which can be contacted with a blood sample to prevent coagulation. For example, an effective amount of a compound of the invention can be contacted with a freshly drawn blood sample to prevent coagulation of the blood sample. As used herein, the term "effective amount" when used in reference to a compound of the invention means an amount of a compound that inhibits factor VIIa activity. The skilled artisan would recognize that an effective amount of a compound of the invention can be determined using the methods disclosed herein (see Example 22) or otherwise known in the art. In view of the disclosed utility of a compound of the invention, the skilled artisan also would recognize that an agent such as heparin can be replaced with a compound of the invention. Such a use of a compound of the invention can result, for example, in a cost saving as compared to other anticoagulants.

In addition, a compound of the invention can be administered to an individual for the treatment of a variety of clinical conditions, including the treatment of a cardiovascular disorder or a complication associated with infection or surgery. Examples of cardiovascular disorders include restenosis following angioplasty, adult respiratory distress syndrome, multi-organ failure, stroke, and disseminated intravascular coagulation clotting disorder. Examples of related complications associated with surgery include deep vein and proximal vein thrombosis, which can occur following surgery. Thus, a compound of the invention is useful as a medicament for reducing or inhibiting unwanted coagulation in an individual.

Since a compound of the invention can inhibit factor VIIa activity, such a compound can in general be useful for reducing or inhibiting blood clotting in an individual. As used herein, the term "individual" means a vertebrate, including a mammal such as a human, in which factor VIIa is involved in the clotting cascade.

Blood clotting in an individual can be reduced or inhibited by administering to the individual a therapeutically effective amount of a compound of the invention. As used herein, the term "therapeutically effective amount" means the dose of a compound that must be administered to an individual in order to inhibit factor VIIa activity in the individual. More specifically, a therapeutically effective amount of a compound of the invention inhibits factor VIIa catalytic activity either directly, within the prothrombinase complex or as a soluble subunit, or indirectly, by inhibiting the assembly of factor VIIa into the prothrombinase complex. Preferred compounds can inhibit factor VIIa activity with a Ki 500 nM, and more preferred compounds with a Ki 50 nM. A therapeutically effective amount can be determined using the methods described, for example, in Example 22 or otherwise known in the art.

In the practice of a therapeutic method of the invention, the particular dosage to obtain a therapeutically effective amount of a pharmaceutical composition to be administered to the individual will depend on a variety of considerations, including, for example, the nature or severity of the disease, the schedule of administration and the age and physical characteristics of the individual. An appropriate dosage can be established using clinical approaches well known in the medical art. Thus, the invention provides a method of specifically inhibiting factor VIIa activity by contacting factor VIIa with a compound having the formula R1—A—B—D—$E_n$—R2. The invention further provides a method of reducing or inhibiting the formation of a blood clot in an individual by administering a therapeutically effective amount of a compound of the invention.

A compound of the invention generally will be administered to an individual as a composition containing one or more compounds of the formula I and a pharmaceutically acceptable carrier. The term "pharmaceutically acceptable carrier" refers to a medium or composition that is nontoxic to an individual or has acceptable toxicity as determined by the appropriate regulatory agency. As used herein, the term pharmaceutically acceptable carrier encompasses any of the standard pharmaceutical carriers comprising solid carrier substances (such as corn starch, lactose, fats, and waxes) or liquids (such as phosphate buffered saline or water), emulsions (such as oil/water or water/oil emulsions), and/or usual additives (for example any of various types of wetting agents). Suitable pharmaceutical carriers and their formulations are described by Martin in Remington's Pharmaceutical Sciences, 15th ed. (Mack Publishing Co., Easton, 1975), which is incorporated herein by reference. Such compositions will, in general, contain a therapeutically effective amount of a compound of the invention together with a suitable amount of carrier so as to comprise the proper dosage for administration to an individual. Thus, the claimed compounds can be useful as medicaments for inhibiting factor VIIa activity and blood clotting in an individual.

The pharmaceutical compositions or medicaments of the invention can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, (such as in the form of suppositories), parenterally, (such as intravenously, intramuscularly or subcutaneously, in the form of injection solutions or infusion solutions, microcapsules, implants, or rods), percutaneously, or topically (such as in the form of ointments, solutions or tinctures), or in other ways, for example in the form of aerosols or nasal sprays. The amount of the active ingredient of the formula I or its pharmaceutically acceptable salt or derivative in a unit dose of a pharmaceutical composition usually is from about 0.5 mg to about 1000 mg, preferably from about 1 mg to about 500 mg, but depending on the type of the pharmaceutical composition the amount may also be higher. The daily dose of the compounds of the formula I that is to be administered can be a single daily dose or can be divided into several (e.g., two, three, four, or more) part administrations.

Pharmaceutically acceptable carriers also can include, for example, other mediums, compounds or modifications to a factor VIIa inhibitor compound of the formula I that enhances its pharmacological function. A pharmaceutically acceptable medium can include, for example, a pharmaceutically acceptable salt. An acid addition salt of a compound of the formula I can be formed, for example, with an inorganic acid (such as hydrochloric acid, hydrobromic acid, phosphoric acid, sulfuric acid or perchloric acid,), with an organic carboxylic acid (such as acetic acid, oxalic acid, maleic acid, malic acid, formic acid, lactic acid, tartaric acid, citric acid, succinic acid, or malonic acid), with an organic sulfonic acid (such as methanesulfonic acid or p-toluenesulfonic acid). An acid group in a compound of the formula 1, for example a carboxylic acid group, can be present as a metal salt the cation of which is based on the alkali and alkaline earth metals (such as sodium, lithium, potassium, calcium, or magnesium) or as a non-toxic ammonium salt (including quaternary ammonium salts and acid addition salts with amines, for example as ammonium, methylammonium, dimethylammonium, trimethylammonium, tetramethylammonium, ethylammonium, triethylammonium or tetraethylammonium salt).

Examples of modifications that enhance the pharmacological function of the compound include, for example, esterification such as the formation of ($C_1$–$C_6$)-alkyl esters (preferably ($C_1$–$C_4$)alkyl esters), wherein the alkyl group is a straight or branched chain. Other acceptable esters include, for example, ($C_5$–$C_7$)-cycloalkyl esters and arylalkyl esters (such as benzyl esters). Such esters can be prepared from the compounds described herein using conventional methods well known in the art of peptide chemistry.

Pharmaceutically acceptable modifications also can include the formation of peptide amides. Such amide modifications, which can be effected upon the compounds of the invention, include those derived from ammonia, primary ($C_1$–$C_6$)-alkylamines, and secondary di-($C_1$–$C_6$)-alkylamines, where the alkyl groups are straight or branched chain, or arylamines having various substitutions. In the case of secondary amines, the amine also can be in the form of a 5- or 6-membered heterocycle which can contain an unsubstituted or substituted nitrogen atom or an oxygen atom or a sulfur atom in addition to the amide nitrogen atom. Methods for preparing such amides are well known in the art.

In another embodiment of the invention, a compound of the invention can be used in an assay to identify the presence of factor VIIa or to isolate factor VIIa in a substantially purified form. Preferably, the compound of the invention is labeled with, for example, a radioisotope, and the labeled compound is detected using a routine method useful for detecting the particular label. In addition, a compound of the invention can be used advantageously as a probe to detect the location or amount of factor VIIa activity in vivo, in vitro, or ex vivo.

It is understood that modifications that do not substantially affect the activity of the various embodiments of this invention are included within the invention disclosed herein. Accordingly, the following examples are intended to illustrate but not to limit the present invention.

EXAMPLE 1
Peptide Synthesis Procedures and General Synthesis Procedures

Starting materials used in the synthesis were obtained from chemical vendors such as Aldrich, Sigma, Fluka, Nova Biochem, and Advanced Chemtech. During the synthesis, the functional groups of the amino acid derivatives used were protected by blocking groups to prevent side reaction during the coupling steps. Examples of suitable protecting groups and their use are described in The Peptides, supra, 1981, and in vol. 9, Udenfriend and Meienhofer (eds.), 1987, which are incorporated herein by reference.

General solid-phase peptide synthesis was used to produce the compounds of the invention. Such methods are described, for example, by Steward and Young, Solid Phase Peptide Synthesis (Freeman & Co., San Francisco, 1969), which is incorporated herein by reference.

Unless indicated otherwise, peptides were synthesized on TentaGel S $NH_2$ Resin (Rapp Polymere, Tübingen, Germany). An acid sensitive linker p-[(R,S)-α-[1-(9H-fluoren-9-yl)methoxyformamido]-2,4-dimethoxybenzyl] phenoxyacetic acid (Knorr Linker) was coupled to the solid support (Bernatowicz et. al, Tetr. Lett. 30 (1989) 4645, which is incorporated herein by reference). Alternatively, peptides were synthesized on polystyrene resin cross-linked with 1% divinylbenzene modified with an acid sensitive linker (Rink resin) (Rink, Tetr. Lett. 28 (1987) 3787; Sieber, Tetr. Lett. 28 (1987) 2107, each of which is incorporated herein by reference). When peptides were synthesized by first coupling the side chain carboxylic acid of a compound of the formula Fmoc-B1—CHR97—C(O)OPG to the resin, TentaGel S $NH_2$ resin modified by attachment of the HMPA linker was employed. Coupling was performed using N,N'-diisopropylcarbodiimide (DIC) in the presence of an equivalent amount of HOBt, with the exception of Alloc-pAph-OH, where 2 equivalents "eq." of HOBt were used. All couplings were done in either N,N-dimethylformamide (DMF) or DMF/DMSO (1/1 mixture) at room temperature "RT". Completion of coupling was monitored by ninhydrin test. A second (double) coupling was performed where coupling in the first instance was incomplete.

Deprotection of the Fmoc group was accomplished using 50% piperidine in DMF for 2+10 min. The amount of Fmoc released was determined from the absorbance at 300 nm of the solution after deprotection, volume of washes and weight of the resin used in the synthesis.

The cycle of each coupling was as follows:

| Step | Action/Reagent | Solvent |
|---|---|---|
| 1. | 0.5 g of functionalized peptide resin | |
| 2. | 3 fold-excess of amino acid derivative/HOBt/DIC | 4 ml DMF |
| 3. | Couple (min. 1 h) | |
| 4. | Wash (3 × 5 ml) | DMF |
| 5. | Ninhydrin test | |
| 6. | Deprotection (2 + 10 min) Piperidine/DMF | 5 ml 50% |
| 7. | Wash (6 × 5 ml) | DMF |
| 8. | Repeat starting at step 2 | |

After completion of peptide assembly on the resin, the final Fmoc deprotection, if necessary, was performed. The peptide resin was then washed successively with DMF and DCM and the peptide was then cleaved and deprotected by a mixture TFA/thioanisole (95/5) for 1.5 hours, unless specified otherwise. The resin was washed with DCM and the DCM wash combined with the TFA releasate. The solution was evaporated, the product precipitated by anhydrous diethyl ether and the solid precipitate was isolated by filtration or centrifugation and dried in vacuo over pellets of solid KOH. The solid was redissolved in a mixture of water and acetonitrile and lyophilized.

The dried peptide was subjected to HPLC purification using an appropriate gradient of 0.1% TFA in water and acetonitrile (ACN). After collecting the peak containing the intended synthetic product, the peptide solution was lyophilized and the peptide was subjected to an identification process, which included electrospray MS and/or NMR and/or amino acid analysis to confirm that the correct compound was synthesized.

For HPLC analysis, a sample of the product was analyzed using Beckman HPLC system (consisting of 126 Solvent Deliver System, 166 Programmable Detector Module 507e Autosampler, controlled by Data Station with Gold Nouveau software) and YMC ODS-AM 4.6×250 mm column at 230 nm and flow rate 1 ml/min.

For product purification, a sample of crude lyophilized peptide was dissolved in a mixture of 0.1% aqueous TFA containing 10% to 50% ACN. The peptide solution usually was filtered through a syringe connected to a 0.45 μm "ACRODISC" 13 CR PTFE (Gelman Sciences; Ann Arbor Mich.) filter. A proper volume of filtered peptide solution was injected into a semi-preparative C18 column (Vydac Protein and Peptide C18, 218TP1022 (22×250 mm); The Separation Group; Hesperia Calif., or YMC ODS-A column (20×250 mm), YMC, Inc., Wilmington, N.C.). The flow rate of a gradient or isocratic mixture of 0.1% TFA buffer and ACN (HPLC grade) as an eluent was maintained using a Beckman "SYSTEM GOLD" HPLC (Beckman, System Gold, Programmable Solvent Module 126 and Programmable Detector Module 166 controlled by "SYSTEM GOLD" software). Elution of the peptide was monitored by UV detection at 230 nm. After identifying the peak corresponding to the compound under synthesis using MS, the compound was collected, lyophilized and biologically tested. MS was performed using a VG Platform (Fisons Instruments) instrument in ES+ mode. For NMR, typically samples were measured in DMSO-$d_6$ (Aldrich) using a Bruker Avance DPX 300 instrument.

EXAMPLE 2
Synthesis of Alloc-pAph-OH

The procedure described below in Example 2 is also applicable to Alloc-D-pAph-OH.

Alloc-Phe(4-CN)—OH 5.7 g (30 mmol) of H-Phe(4-CN)—OH were dissolved in 100 ml of 1M NaOH with addition of 2M NaOH to pH=10 with ice cooling. With vigorous stirring, allyl chloroformate (7.5 ml) was slowly added (pH kept at 10 by 2M NaOH). The reaction mixture was stirred at 0° C. for 15 min and at RT for 30 min, acidified with HCl to pH=2, extracted with ethyl acetate (3 times), dried with $MgSO_4$, and evaporated. The residue was recrystallized from ethyl acetate/hexane to give a white solid. Yield: 7.0 g (85%).

Alloc-Phe[4-C(=S)—$NH_2$]—OH 2.74 g of Alloc-Phe(4-CN)—OH was dissolved in mixture a of pyridine (50 ml) and triethylamine (20 ml) and $H_2S$ was passed through for 30 min. The reaction mixture was kept overnight at RT and evaporated. Drying on high vacuum gave 3.21 g of a solid foam of the crude thioamide, which was directly converted to the methylthioimidate.

Alloc-Phe[4-C(=NH)—$SCH_3$]—OH.HI 1 g of Alloc-Phe[4-C(=S)—$NH_2$]—OH was dissolved in acetone (50 ml) and methyl iodide (5 ml) was added. The reaction mixture was kept overnight at RT, volatile solvents evaporated (fast, 35° C. max.) and the residue treated with diethyl ether. After 1 hour at 0° C., the ether was decanted, the product washed with diethyl ether and dried in vacuo. A yellow solid foam was obtained which was directly converted into the amidine.

Alloc-pAph-OH

All of the Alloc-Phe(4-C(=NH)—$SCH_3$)—OH.HI above was dissolved in 50 ml methanol with 300 µl of acetic acid, and 0.5 g of ammonium acetate was added. The mixture was heated for 3 hours to 55° C., evaporated, and 10 ml of acetone was added. After 2 hours at 0° C., the solid product was filtered, washed with a little cold acetone, a little cold methanol and diethyl ether, and dried in vacuo to give a yellowish solid. Yield: 0.53 g.

EXAMPLE 3
Synthesis of Alloc-pAph-Glu-Arg-Cha-$NH_2$

To 1 g of TentaGel S $NH_2$ resin (substitution 0.26 mmol/g), Knorr amide linker was attached. According to the general procedures outlined in Example 1, the following protected amino acids were coupled: Fmoc-Cha-OH, Fmoc-Arg(Pmc)-OH, Fmoc-Glu(OtBu)-OH and Alloc-pAph. The peptide was cleaved and deprotected by TFA/thioanisole (95/5) for 3 hours and processed as described in Example 1. The crude compound was purified using HPLC as described in Example 1 and characterized bit MS. $(M+H)^+$: found 729.1, calc. 729.4.

EXAMPLE 4
Synthesis of allyl-NH—C(O)-pAph-Glu-Arg-Cha-$NH_2$

To 0.5 g of TentaGel S $NH_2$ resin (substitution 0.26 mmollg), Knorr amide linker was attached. According to the general procedures in Example 1, the following protected amino acids were coupled: Fmoc-Cha-OH, Fmoc-Arg(Pmc)-OH, Fmoc-Glu(OtBu)-OH and Fmoc-Phe(4-CN). After N-terminal Fmoc deprotection, the resin was treated with a solution of 1 mmol of allyl isocyanate in 3 ml of DMF for 2 hours. The resin was then washed with DMF, and triethylamine/pyridine (1/2) and treated with a saturated solution of $H_2S$ in pyridine/triethylamine overnight. The resin was washed with acetone and the thioamide resin was reacted with methyl iodide (3 ml of 10% solution of methyl iodide in acetone) for 6 hours. The methylthioimidate resin was washed with acetone, methanol and treated with solution of 0.2 g ammonium acetate, 100 µl acetic acid in 3 ml of methanol at 55° C. for 3 hours. The resin was washed with methanol, DMF and DCM and the peptide was cleaved and deprotected by TFA/thioanisole (95/5) for 3 hours and processed as described in Example 1. The crude material was purified using HPLC as described in Example 1 and characterized by MS. $(M+H)^+$: found 728.3, calc. 728.4.

EXAMPLE 5
Synthesis of Alloc-pAph-Glu-Arg-Chg-$NH_2$

To 1 g of TentaGel S $NH_2$ resin (substitution 0.26 mmol/g), Knorr amide linker was attached. According to the general procedures in Example 1, the following protected amino acids were coupled: Fmoc-Chg-OH, Fmoc-Arg(Pmc)-OH, Fmoc-Glu(OtBu)-OH and Alloc-pAph. The peptide was cleaved and deprotected by TFA/thioanisole (95/5) for 3 hours and processed as described in Example 1. The crude compound was purified using HPLC as described in Example 1 and characterized by MS. $(M+H)^+$: found 715.8, calc. 715.4.

EXAMPLE 6
Synthesis of Alloc-D-pAph-Glu-Arg-Cha-$NH_2$

To 1 g of TentaGel S $NH_2$ resin (substitution 0.26 mmol/g), Knorr amide linker was attached. According to the general procedures in Example 1, the following protected amino acids were coupled: Fmoc-Cha-OH, Fmoc-Arg(Pmc)-OH, Fmoc-Glu(OtBu)-OH and Alloc-D-pAph-OH (synthesized according to the same procedure as Alloc-pAph-OH in Example 2). The peptide was cleaved and deprotected by TFA/thioanisole (95/5) for 3 hours and processed as described in Example 1. The crude compound was purified using HPLC as described in Example 1 and characterized by MS. $(M+H)^+$: found 729.2, calc. 729.4.

EXAMPLE 7
Synthesis of Alloc-pAph-Glu-Phe(4-guanidino)-Cha-$NH_2$

To 0.25 g of TentaGel S $NH_2$ resin (substitution 0.23 mmol/g), Knorr amide linker was attached. According to the general procedures in Example 1, the following protected amino acids were coupled: Fmoc-Cha-OH, Fmoc-Phe(4-NH—C(=NBoc)-NH-Boc)-OH, Fmoc-Glu(OtBu)-OH and Alloc-pAph-OH. The peptide was cleaved and deprotected by TFA/thioanisole (95/5) for 1 hour and processed as described in Example 1. The crude compound was purified using HPLC as described in Example 1 and characterized by MS. $(M+H)^+$: found 777.1, calc. 777.4

EXAMPLE 8
Synthesis of Alloc-pAph-Glu-Dap[—C(=NH)—NH$_2$]-Cha-NH$_2$

To 0.25 g of TentaGel S NH$_2$ resin (substitution 0.23 mmol/g), Knorr amide linker was attached. According to the general procedures in Example 1, the following protected amino acids were coupled: Fmoc-Cha-OH, Fmoc-Dap[—C(=N-Boc)-NH-Boc]-OH, Fmoc-Glu(OtBu)-OH and Alloc-pAph-OH. The peptide was cleaved and deprotected by TFA/thioanisole (95/5) for 1 hour and processed as described in Example 1. The crude compound was purified using HPLC as described in Example 1 and characterized by MS. (M+H)$^+$: found 729.1, calc. 729.4.

EXAMPLE 9
Synthesis of Alloc-pAph-Glu-Dap[—C(=NH)—CH$_3$]-Cha-NH$_2$

To 0.25 g of TentaGel S NH$_2$ resin (substitution 0.26 mmol/g), Knorr amide linker was attached. According to the general procedures in Example 1, the following protected amino acids were coupled: Fmoc-Cha-OH, Fmoc-Dap(Alloc)-OH and Fmoc-Glu(OtBu)-OH. With the N-terminal Fmoc-protecting group attached, the resin was washed with a DMF/NMM/AcOH (5/0.5/1) mixture, and under constant mixing with a stream of argon, the Alloc group was deprotected by addition of 100 mg of Pd(P(Ph)$_3$)$_4$ over a period of 3 hours. The resin was washed with DMF and treated with solution of 150 mg of 2-methyinaphthyl acetthioimidate in 4 ml of ethanol/DMSO (3/1) for 1 hour. After washing with DMF, the Fmoc group was deprotected (1+5 min) and the N-terminal Alloc-pAph-OH was coupled. The peptide was cleaved and deprotected by TFA/thioanisole (95/5) for 1 hour and processed as described in Example 1. The crude compound was purified using HPLC as described in Example 1 and characterized by MS. (M+H)$^+$: found 700.1, calc. 700.4.

EXAMPLE 10
Synthesis of Alloc-pAph-Glu-Ala[3-C(=NH)—NH$_2$]-Cha-NH$_2$

To 0.25 g of TentaGel S NH$_2$ resin (substitution 0.26 mmol/g), Knorr amide linker was attached. According to the general procedures in Example 1, the following protected amino acids were coupled: Fmoc-Cha-OH, Fmoc-Ala(3-CN)—OH, Fmoc-Glu(OtBu)-OH and Alloc-Phe(4-CN)—OH. A mixture of pyridine and triethylamine (2/1) was saturated with H$_2$S (RT, 15–30 min), and this solution added to the resin prewashed with pyridine/triethylamine (2/1). After standing overnight, the resin was washed with acetone and treated with a solution of 20% methyl iodide in acetone overnight. The resin was then washed with acetone and methanol. The resin bound methylthioimidate was then converted into the amidine by heating (waterbath, 55° C., 3 hours) of the resin with a solution of 10 eq. of ammonium acetate in methanol containing 5% acetic acid. After this final conversion, the resin was washed with methanol, DMF, and DCM. The peptide was cleaved and deprotected by TFA/thioanisole (95/5) for 1 hour and processed as described in Example 1. The crude compound was purified using HPLC as described in Example 1 and characterized by MS. (M+H)$^+$: found 685.9, calc. 686.4.

EXAMPLE 11
Synthesis of Alloc-pAph-Glu-Asn-Cha-NH$_2$

To 0.125 g of Rink resin (substitution 0.78 mmol/g), after Fmoc-deprotection the following protected amino acids were coupled according to the general procedures described in Example 1: Fmoc-Cha-OH, Fmoc-Asn-OH, Fmoc-Glu(OtBu)-OH, and Alloc-pAph-OH. The peptide was cleaved and deprotected by TFA/thioanisole (95/5) for 1 hour and processed as described in Example 1. The crude compound was purified using HPLC as described in Example 1 and characterized by MS. (M+H)$^+$: found 686.9, calc. 687.3

EXAMPLE 12
Synthesis of Alloc-pAph-Glu-Dab-Cha-NH$_2$

To 0.25 g of TentaGel S NH$_2$ resin (substitution 0.26 mmol/g), Knorr amide linker was attached. According to the general procedures in Example 1, the following protected amino acids were coupled: Fmoc-Cha-OH, Fmoc-Dab(Boc)-OH, Fmoc-Glu(OtBu)-OH and Alloc-pAph. The peptide was cleaved and deprotected by TFA/thioanisole (95/5) for 1 hour and processed as described in Example 1. The crude compound was purified using HPLC as described in Example 1 and characterized by MS. (M+H)$^+$: found 673.2, calc. 673.4.

EXAMPLE 13
Synthesis of Alloc-pAph-Glu-Ala[3-C(=NH)—NH$_2$]—NH$_2$

To 0.25 g of TentaGel S NH$_2$ resin (substitution 0.26 mmol/g), Knorr amide linker was attached. According to the general procedures in Example 1, the following protected amino acids were coupled: Fmoc-Ala(3-CN)—OH, Fmoc-Glu(OtBu)-OH and Alloc-Phe(4-CN)—OH. A mixture of pyridine and triethylamine (2/1) was saturated with H$_2$S (RT, 15–30 min) and this solution added to the resin prewashed with pyridine/triethylamine (2/1). After standing overnight, the resin was washed with acetone and treated with a solution of 20% methyl iodide in acetone overnight. The resin was then washed with acetone and methanol. The resin bound methylthioimidate was then converted into the amidine by heating (55° C., waterbath, 3 hours) of the resin with solution of 10 eq. of ammonium acetate in methanol containing 5% acetic acid. After this final conversion, the resin was washed with methanol, DMF, and DCM. The peptide was cleaved and deprotected by TFA/thioanisole (95/5) for 1 hour and processed as described in Example 1. The crude compound was purified using HPLC as described in Example 1 and characterized by MS. (M+H)$^+$: found 533.3, calc. 533.2.

EXAMPLE 14
Synthesis of Alloc-pAph-Glu-Gly-Cha-NH$_2$

To 0.150 g of Rink resin (substitution 0.78 mmol/g), after Fmoc-deprotection, the following protected amino acids were coupled according to the general procedure described in Example 1: Fmoc-Cha-OH, Fmoc-Gly-OH, Fmoc-Glu(OtBu)-OH and Alloc-pAph-OH. The peptide was cleaved and deprotected by TFA/thioanisole (95/5) for 1 hour and processed as described in Example 1. The crude compound was purified using HPLC as described in Example 1 and characterized by MS. (M+H)$^+$: found 630.1, calc. 630.3.

EXAMPLE 15
Synthesis of Alloc-pAph-Glu-Asn-(Ph—CH$_2$—CH$_2$—)Gly-NH$_2$

For N-substituted glycines, the procedure of Zuckermann et al. (J. Am. Chem. Soc. 114 (1992) 10646, which is incorporated herein by reference) was used. To 0.1 g of Rink resin (substitution 0.78 mmol/g), after Fmoc-deprotection, bromoacetic acid was coupled via the symmetrical anhydride in DCM/DMF. After 10 minutes, the resin was washed with DCM and the coupling repeated once more. After washing with DCM and DMF, the resin was treated with a 1M solution of 2-phenylethylamine in DMSO overnight.

After washing with DMF, the resin now carrying the residue (Ph—CH₂—CH₂—)NH—CH₂—C(O) attached to the linker was reacted with the symmetrical anhydride of Fmoc-Asn(Trt)-OH in DCM/DMF. After Fmoc-deprotection, according to the the general procedures in Example 1, the following protected amino acids were coupled: Fmoc-Glu(OtBu)-OH and Alloc-pAph-OH. The peptide was cleaved and deprotected by TFA/thioanisole (95/5) for 1 hour and processed as described in Example 1. The crude compound was purified using HPLC as described in Example 1 and characterized by MS. (M+H)⁺: found 694.9, calc. 695.3

EXAMPLE 16
Synthesis of Alloc-pAph-Glu-Thr(Bzl)-NH—CH₂—CH₂—CH(Ph)₂

H-Thr(Bzl)-NH—CH₂—CH₂—CH(Ph)₂.HCl 0.62 g (2 mmol) of Boc-Thr(Bzl)-OH were dissolved in 10 ml DCM, 2 mmol of triethylamine were added and the solution was cooled to 0° C. With stirring, 2 mmol of isobutyl chloroformate were slowly added. The cooling bath was removed, the solution was stirred for 15 minutes and 2.5 mmol of 3,3-diphenylpropylamine in 2 ml of DMF were added and stirred at room temperature for 1 hour. The solution was evaporated, dissolved in ethyl acetate and extracted with 0.5M KHSO₄ solution, sat. NaHCO₃ solution and brine, dried with MgSO₄ and evaporated. The oily product was dissolved in 10 ml of DCM, and 10 ml of a 4M solution of hydrochloric acid in dioxane were added. After 10 minutes the solvents were evaporated, the product hydrochloride was precipitated with diethyl ether, filtered off, washed with diethyl ether and dried in vacuo to give a white solid. MS analysis: (M+H)⁺: found 403.1, calc. 403.2.

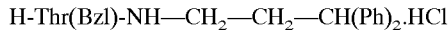
Alloc-pAph-Glu-Thr(Bzl)-NH—CH₂—CH₂—CH(Ph)₂

To 0.5 g of TentaGel S NH₂ resin (substitution 0.26 mmol/g), 4-hydroxymethylphenoxyacetic acid was attached (3 eq., activated with DIC/HOBt for 1.5 h). Fmoc-Glu(OH)—O-allyl was attached to the resin via side chain using DIC/HOBt/NMI in DMF overnight. The allyl protecting group was removed by shaking the resin with Pd(PPh₃)₄ in DMF/AcOH/NMM (10/2/1) for 4 h under argon. The deprotected carboxy group was activated with a solution of 0.5 mmol BOP, 0.5 mmol HOBt, 1.5 mmol DIEA and 0.5 mmol of of H-Thr(Bzl)-NH—CH₂—CH₂—CH(Ph)₂.HCl in 1.5 ml of DMF for 2 hours. After Fmoc deprotection, Alloc-pAph-OH was coupled according to the general procedure in Example 1. The peptide was cleaved and deprotected by TFA/thioanisole (95/5) for 1.5 hours and processed as described in Example 1. The crude compound was purified using HPLC as described in Example 1 and characterized by MS. (M+H)⁺: found 805.0, calc. 805.4.

EXAMPLE 17
Synthesis of Alloc-pAph-Glu-Dab-NH—CH₂—CH₂—Ph

To 0.2 g of TentaGel S NH₂ resin (substitution 0.26 mmol/g), 4-hydroxymethyl phenoxyacetic acid was attached (2.5 eq., activated with DIC/HOBt for 4 h). The hydroxy group was substituted with bromine by treatment of the resin with CBr₄ (5 eq.)/PPh₃ (5 eq.) in DCM for 4 h. The bromine derivatized resin was treated with a 2M solution of phenylethylamine in DCM overnight. Fmoc-Dab(Boc)-OH was coupled to the resin using TFFH/DIEA (acyl fluoride generated in situ). According to the general procedure in Example 1, the following protected amino acids were coupled: Fmoc-Glu(OtBu)-OH and Alloc-pAph-OH. The peptide was cleaved and deprotected with TFA/triisopropylsilane (99/1) for 2 h. TFA was evaporated, the peptide was dissolved in H₂O/ACN and lyophilized. The crude material was purified using HPLC as described in Example 1 and characterized by MS. (M+H)⁺: found 624.2, calc. 624.3.

EXAMPLE 18
Synthesis of Alloc-pAph-Glu-NH—CH₂—CH₂—CN

To 0.2 g of TentaGel S NH₂ resin (substitution 0.26 mmol/g), 4-hydroxymethyl phenoxyacetic acid was attached (3 eq., activated with DIC/HOBt for 1.5 h). Fmoc-Glu(OH)—O-allyl was attached to the resin via the side chain using DIC/HOBt/NMI in DMF overnight. The allyl protecting group was removed by shaking the resin with Pd(PPh₃)₄ in DMF/AcOH/NMM (10/2/1) for 4 h under argon. The deprotected carboxy group was activated with DIC (3 eq.)/HOBt (3 eq.) for 10 min and 2-cyanoethylamine (3 eq.) in DMF was added to the resin for 3 h. After Fmoc deprotection, Alloc-pAph-OH was coupled according to the general procedure in Example 1. The peptide was cleaved and deprotected with TFA/triisopropylsilane (99/1) for 2 h. TFA was evaporated, the peptide was dissolved in H₂O/ACN and lyophilized. The crude material was purified using HPLC as described in Example 1 and characterized by MS. (M+H)⁺: found 473.1, calc. 473.2.

EXAMPLE 19
Synthesis of Alloc-pAph-Glu-Asn-NH—CH₂-Chx

To 0.1 g of TentaGel S NH₂ (substitution 0.26 mmol/g) Knorr amide linker was attached. Fmoc-Asp(OH)—O-allyl was coupled to the linker via the side chain and the allyl protecting group was removed as in Example 18. The deprotected carboxy group was activated with DIC (5 eq.)/HOBt (5 eq.) and cyclohexylmethylamine (5 eq.) in DMF was added for 2.5 h. After Fmoc deprotection, Fmoc-Glu(OtBu)-OH and Alloc-pAph-OH was coupled according to the general procedure in Example 1. The peptide was cleaved and deprotected with TFA/triisopropylsilane (99/1) for 2 h. TFA was evaporated, the peptide was dissolved in H₂O/ACN and lyophilized. The crude material was purified using HPLC as described in Example 1 and characterized by MS. (M+H)⁺: found 629.9, calc. 630.3.

EXAMPLE 20
Synthesis of Alloc-pAph-Glu-Asn-NH—CH₂—CH₂—Ph

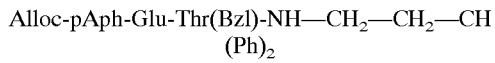
2-(S)-[2-(S)-Allyloxycarbonylamino-3-(4-carbamimidoyl-phenyl)-propionylamino]-pentanedioic acid 5-tert-butyl ester 1-methyl ester hydrochloride To 2-(S)allyloxycarbonylamino-3-(4-carbamimidoyl-phenyl)-propionic acid hydrochloride (3.48 g, 10.6 mmol) and 2-(S)-amino-pentanedioic acid 5-tert-butyl ester 1-methyl ester hydrochloride (2.7 g, 10.6 mmol) in 20 ml of DMF were added at −15° C. TOTU (3.83 g, 11.67 mmol) and N-ethylmorpholine (2.7 ml, 21.2 mmol). The mixture was stirred for 1 hour and then allowed to warm to room temperature. After evaporation, ethyl acetate was added to the residue and the organic layer was extracted with aqueous sodium hydrogen carbonate solution, potassium hydrogen sulfate solution, and water. The organic layer was evaporated. Yield: 2.8 g (50%). MS: m/z=491.3 (M+H)⁺.

2-(S)-[2-(S)-Allyloxycarbonylamino-3-(4-carbamimidoyl-phenyl)-propionylamino]-pentanedioic acid 5-tert-butyl ester To 2-(S)-[2-(S)-allyloxycarbonylamino-3-(4-carbamimidoyl-phenyl)-propionylamino]-pentanedioic acid 5-tert-butyl ester 1-methyl ester hydrochloride (3.06 g, 5.8 mmol) in 100 ml of water and 30 ml of THF was added lithium hydroxide hydrate (0.49 g, 11.6 mmol). The solution was stirred at room temperature for 12 hours, evaporated, and freeze-dried. The residue was purified by chromatography on Sephadex LH20 employing n-butanol/glacial acetic acid/water (17/1/2) as eluent. Pure fractions were combined. The solvent was evaporated, the residue was taken up in water, and the aqueous solution was freeze-dried. Yield: 2.7 g (97%). MS: m/z=477.4 (M+H)$^+$.

4-(S)-[2-(S)-Allyloxycarbonylamino-3-(4-carbamimidoyl-phenyl)-propionylamino]-4-(2-carbamoyl-1-(S)-(2-phenylethylcarbamoyl)-ethylcarbamoyl)-butyric acid hydrochloride (Alloc-pAph-Glu-Asn-NH—CH$_2$—CH$_2$—Ph)

To 2-(S)-[2-(S)-allyloxycarbonylamino-3-(4-carbamimidoyl-phenyl)-propionylamino]-pentanedioic acid 5-tert-butyl ester (48 mg, 0.1 mmol) and 2-(S)-amino-N1-phenylethyl-succinamide hydrochloride (27 mg, 0.1 mmol) in 5 ml of DMF were added at 0° C. HATU (39 mg, 0.1 mmol) and collidine (24.2 mg, 0.2 mmol). The mixture was stirred for 1 hour and then allowed to warm to room temperature. After evaporation the residue was purified by chromatography on Sephadex LH20 employing n-butanol/glacial acetic acid/water (17/1/2) as eluent. Pure fractions were combined. The solvent was evaporated, the residue was taken up in water and the aqueous solution was freeze-dried. Yield: 45 mg (66%). MS: m/z=638.4 (M+H)$^+$.

EXAMPLE 21

Synthesis of Alloc-pAph-Glu-Asn-NH-(3-chlorobenzyl)

To 2-(S)-[2-(S)-allyloxycarbonylamino3-(4-carbamimidoyl-phenyl)-propionylamino]-pentanedioic acid 5-tert-butyl ester (50 mg, 0.105 mmol) and 2-(S)-amino-N1-(3-chlorobenzyl)succinamide trifluoroacetate (61 mg, 0.16 mmol) in 5 ml of DMF were added at 0° C. TOTU (36 mg, 0.11 mmol) and N-ethylmorpholine (57 μl, 0.4 mmol). The mixture was stirred for 1 hour and then allowed to warm to room temperature. After evaporation, the residue was purified by chromatography on Sephadex LH20 employing n-butanol/glacial acetic acid/water (17/1/2) as eluent. Pure fractions were combined. The solvent was evaporated, the residue was taken up in water, and the aqueous solution was freeze-dried. Yield of 4-(S)-[2-(S)-allyloxycarbonylamino-3-(4-carbamimidoyl-phenyl)-propionylamino]4-(2-carbamoyl-1-(S)-(3-chlorobenzylcarbamoyl)-ethylcarbamoyl)-butyric acid (Alloc-pAph-Glu-Asn-NH-(3-chlorobenzyl or Alloc-pAph-Glu-Asn-3-chlorobenzylamide): 28 mg (41%). MS:m/z=658.3 (M+H)$^+$.

Further example compounds prepared analogously to the above examples are listed in Table 2 above.

EXAMPLE 22

Determination of Ki for FVIIa Inhibition

The inhibitory activity (Ki) of each compound towards factor VIIIa/tissue factor activity was determined using a chromogenic assay essentially as described previously. J. A. Ostrem, F. Al-Obeidi, P. Safar, A. Safarova, S. K. Stringer, M. Patek, M. T. Cross, J. Spoonamore, J. C. LoCascio, P. Kasireddy, D. S. Thorpe, N. Sepetov, M. Lebi, P. Wildgoose, P. Strop, "Discovery of a novel, potent, and specific family of factor Xa inhibitors via combinatorial chemistry". Biochemistry 37 (1998) 1053–1059. Kinetic assays were conducted at 25° C. in half-area microtiter plates (Costar Corp., Cambridge, Mass.) using a kinetic plate reader (Molecular Devices Spectramax 250). A typical assay consisted of 25 μl of human factor VIIa and TF (5 nM and 10 nM, respective final concentration) combined with 40 μl of inhibitor dilutions in 10% DMSO/TBS-PEG buffer (50 mM Tris, 15 mM NaCl, 5 mM CaCl$_2$; 0.05% PEG 8k, pH 8.15). Following a 15 minute preincubation period, the assay was initiated by the addition of 35 μl of the chromogenic substrate S-2288 (D-Ile-Pro-Arg-pNA, Pharmacia Hepar Inc, 500 μM final concentration.). The apparent inhibition constants were calculated from the slope of the progress curves during the linear part of the time course, typically between 1 and 5 min following addition of substrate to the assay. The true Ki was subsequently determined for each compound by correcting for substrate concentration (S) and the Km using the formula Ki=Ki app/(1+(S)/Km). I. H. Segal, Enzyme Kinetics, pp 100–125 (John Wiley & Sons, N.Y., 1975).

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and equivalency of the claims are to be embraced within their scope.

We claim:

1. A compound of the formula I, in any of its stereoisometric forms or a mixture thereof in any ratio, or a pharmaceutically acceptable salt thereof:

R1—A—B—D—E$_n$—R2     (I)

wherein:

R1 represents
R13,
R12C(O), or
1 to 3 amino acids having an N-terminus, the N-terminus of which is optionally substituted with a substituent chosen from R14C(O), R15S(O)$_2$, and an amino protecting group, wherein:
R12 is chosen from alkyl, alkenyl, alkynyl, alkyloxy, alkylamino, alkenylamino, alkynylamino, alkenyloxy, alkynyloxy, aryl, heteroaryl, heterocycloalkyl, arylalkyl, heteroarylalkyl, heterocycloalkylalkyl, heteroalkyl, heteroalkenyl, and heteroalkynyl, which residues are all optionally substituted,
R13 is chosen from an amino protecting group, hydrogen, alkyl, aryl, arylalkyl, heteroaryl, heteroarylalkyl, heterocycloalkyl, and heterocycloalkylalkyl, and
R14 and R15 are independently chosen from alkyl, aryl, arylalkyl, heteroaryl, heteroarylalkyl, heterocycloalkyl, and heterocycloalkylalkyl;

A is the group A1-A2-A3, wherein:
A1 is NH,
A2 is CHR93, wherein R93 is 4-amidinophenylmethyl, and
A3 is C(O);

B is the group B1-B2-B3, wherein:
B1 is NR95, wherein R95 is chosen from hydrogen and alkyl,
B2 is CHR97, wherein R97 is ethyl which is substituted in the 2-position by a substituent chosen from hydroxycarbonyl, alkyloxycarbonyl, and arylalkyloxycarbonyl, and B3 is C(O);

D is the group D1-D2-D3, wherein:
D1 is NH,
D2 is CR81 R82, wherein R81 and R82 are independently chosen from hydrogen and the unsubstituted or substituted residues alkyl, aryl, arylalkyl, heteroaryl, heteroarylalkyl, heterocycloalkyl, and heterocycloalkylalkyl, and
D3 is C(O);

$E_n$ is $(E1-E2-E3)_n$, wherein:
n is zero, one, two, or three,
E1 is NR70, wherein R70 is chosen from hydrogen, alkyl, aryl, arylalkyl, heteroaryl, heteroarylalkyl, heterocycloalkyl, and heterocycloalkylalkyl,
E2 is CR71R72, wherein R71 and R72 are independently chosen from hydrogen and the unsubstituted or substituted residues alkyl , aryl, arylalkyl, heteroaryl, heteroarylalkyl, heterocycloalkyl, and heterocycloalkylalkyl, and
E3 is C(O); and R2 is chosen from NR21R22, OR23, and R24, wherein R21, R22, R23, and R24 are independently chosen from hydrogen and unsubstituted or substituted residues alkyl, aryl, arylalkyl, heteroaryl, heteroarylalkyl, heterocycloalkyl, and heterocycloalkylalkyl;

wherein alkyl and heteroalkyl contain 1 to 13 carbon atoms, and in a heteroalkyl residue one or more carbon atoms are replaced with heteroatoms chosen from N, O, and S; alkenyl, alkynyl, heteroalkenyl, and heteroalkynyl contain 2 to 13 carbon atoms, and in a heteroalkenyl and heteroalkynyl residue one or more carbon atoms are replaced with heteroatoms chosen from N, O, and S; aryl and heteroaryl contain 5 to 13 ring carbon atoms and in a heteroaryl residue one or more carbon atoms are replaced with heteroatoms chosen from N, O, and S; heterocycloalkyl contains 3 to 8 ring carbon atoms of which one to three carbon atoms are replaced with heteroatoms chosen from N, O, and S.

2. A compound as claimed in claim 1, wherein the residues representing R12 are optionally substituted with substituents chosen from halogen, trifluoromethyl, hydroxy, nitro, amino, cyano, carboxy, aminocarbonyl, alkylsulfonyl, aminosulfonyl, alkyloxy, alkylcarbonylamino, and mono- or dialkylamino.

3. A compound as claimed in claim 1, wherein the residues representing R81 and R82 are optionally independently substituted with substituents chosen from amino, aminocarbonyl, amidino, guanidino, aminoalkyl, hydroxy, mercapto, which are optionally substituted with a protecting group, and acetimido, nitro, and cyano.

4. A compound as claimed in claim 1, wherein the residues representing R71 and R72 are optionally independently substituted with substituents chosen from alkyl, alkyloxy, halogen, trifluoromethyl, nitro, cyano, alkylsulfonyl, alkylcarbonyl, phenylcarbonyl, and 2-phenyl-1,3-dithiolan-2-yl; which substituents are optionally further substituted.

5. A compound as claimed in claim 1, wherein the residues representing R21, R22, R23, and R24 are optionally independently substituted with substituents chosen from halogen, trifluoromethyl, hydroxy, nitro, cyano, alkyloxy, alkylenedioxy, dialkylamino, alkylsulfonyl, aminosulfonyl, and oxo (=O); and these substituents are optionally further substituted.

6. A compound as claimed claim 1, wherein the linear or branched alkyl chains have 1 to 6 carbon atoms, unsaturated linear or branched alkenyl and alkynyl chains have 2 to 6 carbon atoms, and cyclic alkyl groups have 3 to 8 carbon atoms.

7. A compound as claimed in claim 1, wherein R1 is R12C(O) wherein R12 is as defined in claim 1, D is NH—CHR82—C(O) wherein R82 is as defined in claim 1, and $E_n$ is $(E1-E2-E3)_n$ wherein:
n is zero, one, or two,
E1 is NH,
E2 is CHR72, wherein R72 is as defined in claim 1, and
E3 is C(O).

8. A compound as claimed in claim 1, wherein n is zero or one and R2 is NHR22 wherein R22 is as defined in claim 1.

9. A compound as claimed in claim 1, wherein R1 is allyloxycarbonyl or allylaminocarbonyl.

10. A compound as claimed in claim 1, wherein A is (L)-4 amidinophenylalanine.

11. A compound as claimed in claim 1, wherein B is (L)-glutamic acid or a pharmaceutically acceptable salt or ester thereof.

12. A compound as claimed in claim 1, wherein D is a residue chosen from Arg, Dap, Dab, Orn, Lys, Dap[—C(=NH)—NH$_2$], Dab[—C(=NH)—NH$_2$], Lys[—C(=NH)—NH$_2$], Lys[—C(=NH)—CH$_3$], Orn[—C(=NH)—CH$_3$], Dab[—C(=NH)—CH$_3$], Dap[—C(=NH)—CH$_3$], Dab(Alloc), Asn, Gln, Met, Ser, Thr, Ser (Bzl), Thr(Bzl), Cys(Me), Cys(Bzl), Cys(Acm), Arg(NO$_2$), His, Trp, Phg, Gly, Ala, Val, Ile, Leu, Phe, Phe(4-NH—C(=NH)—NH$_2$), Phe(4-NO$_2$), 2-Abu, Ala(3-CN), Ala[3-C(=NH)—NH$_2$], 2-Abu(4-CN), and 2-Abu[4-C(=NH)—NH$_2$].

13. A compound as claimed in claim 1, wherein E is a residue chosen from Cha, Chg, and Phe[4-C(—S—CH$_2$—CH$_2$—S—)—Ph].

14. A compound as claimed in claim 1, wherein R22 is a residue chosen from hydrogen, alkyl, aryl, arylalkyl, heteroarylalkyl, and heterocycloalkylalkyl; which residues are optionally substituted with substituents chosen from halogen, hydroxy, alkyloxy, alkylenedioxy, nitro, cyano, dialkylamino, alkylsulfonyl, aminosulfonyl, and trifluoromethyl, which are all optionally further substituted.

15. A compound as claimed in claim 1, wherein:
R1 is allyloxycarbonyl or allylaminocarbonyl;
A is (L)-4-amidinophenylalanine;
B is (L)-glutamic acid or a pharmaceutically acceptable salt or ester of (L)-glutamic acid;
D is a residue chosen from Arg, Dap, Dab, Orn, Lys, Dap[—C(=NH)—NH$_2$], Dab[—C(=NH)—NH$_2$], Lys[—C(=NH)—NH$_2$], Lys[—C(=NH)—CH$_3$], Orn[—C(=NH)—CH$_3$], Dab[—C(=NH)—CH$_3$], Dap[—C(=NH)—CH$_3$], Dab(Alloc), Asn, Gln, Met, Ser, Thr, Ser(Bzl), Thr(Bzl), Cys(Me), Cys(Bzl), Cys(Acm), Arg(NO$_2$), His, Trp, Phg, Gly, Ala, Val, Ile, Leu, Phe, Phe(4-NO$_2$), Phe(4-NH—C(=NH)—NH$_2$), 2-Abu, Ala(3-CN), Ala[3-C(=NH)—NH$_2$], 2-Abu(4-CN), and 2-Abu[4-C(=NH)—NH$_2$];
n is zero or one;
E is a residue chosen from Cha, Chg, and Phe[4-C(—S—CH$_2$—CH$_2$—S—)—Ph];
R2 is NHR22; and
R22 is hydrogen or a residue chosen from benzyl, naphthylmethyl, pyridylmethyl, phenylethyl, naphthylethyl, pyridylethyl, phenylpropyl, naphthylpropyl, pyridylpropyl, fluorenyl, diphenylmethyl, diphenylethyl and diphenylpropyl, which residues are unsubstituted or substituted with substituents chosen from F, Cl, Br, hydroxy, methoxy, methylenedioxy, nitro, cyano, dialkylamino, alkylsulfonyl, aminosulfonyl, and trifluoromethyl.

16. A composition of matter comprising at least one of the following compounds, or a pharmaceutically acceptable salt, amide, or ester thereof:

Alloc-pAph-Glu-Arg-Cha-NH$_2$,
Allylaminocarbonyl-pAph-Glu-Arg-Cha-NH$_2$,
Alloc-pAph-Glu-Arg-Chg-NH$_2$,
Alloc-pAph-Glu-Dap[—C(=NH)—NH$_2$]-Cha-NH$_2$,
Alloc-pAph-Glu-Ala[3-C(=NH)—NH$_2$]-Cha-NH$_2$,
Alloc-pAph-Glu-Asn-Cha-NH$_2$,
Alloc-pAph-Glu-Dab-Cha-NH$_2$,
Alloc-pAph-Glu-Dap[—C(=NH)—NH$_2$]—NH$_2$,
Alloc-pAph-Glu-Gly-Cha-NH$_2$,
Alloc-pAph-Glu-Thr(Bzl)-NH—(CH$_2$)$_2$—CH(Ph)$_2$,
Alloc-pAph-Glu-Dab-NH—(CH$_2$)$_2$—Ph,
Alloc-pAph-Glu-Asn-NH—CH$_2$-Chx,
Alloc-pAph-Glu-Dap[—C(=NH)—CH$_3$]-Cha-NH$_2$,
Alloc-pAph-Glu-Dab[—C(=NH)—NH$_2$]-Cha-NH$_2$,
Alloc-pAph-Glu-2-Abu(4-CN)-Cha-NH$_2$,
Alloc-pAph-Glu-Ala(3-CN)-Cha-NH$_2$,
Alloc-pAph-Glu-Asn-1-naphthylmethylamide,
Alloc-pAph-Glu-Asn-1-(1-naphthyl)ethylamide,
Alloc-pAph-Glu-Asn-2-naphthylmethylamide,
Alloc-pAph-Glu-Asn-3,4-dichlorobenzylamide,
Alloc-pAph-Glu-Asn-2-(3-chlorophenyl)ethylamide,
Alloc-pAph-Glu-Arg(NO$_2$)-Cha-NH$_2$,
Alloc-pAph-Glu-Cys(Bzl)-Cha-NH$_2$,
Alloc-pAph-Glu-Trp-Cha-NH$_2$,
Alloc-pAph-Glu-Phg-Cha-NH$_2$,
Alloc-pAph-Glu-Asn-9-fluorenylamide,
Alloc-pAph-Glu-Asn-3,5-bistrifluoromethylbenzylamide,
Alloc-pAph-Glu-Dap[—C(=NH)—NH$_2$]-Phe[4-C(—S—(CH$_2$)$_2$—S—)—Ph]—NH$_2$,
Alloc-pAph-Glu-Cys(Bzl)-Cha-NH$_2$,
Alloc-pAph-Glu-Thr(Bzl)-Cha-NH$_2$,
Alloc-pAph-Glu-Phe(4-NO$_2$)-Cha-NH$_2$,
Alloc-pAph-Glu-Asn-3,4-methylenedioxybenzylamide,
Alloc-pAph-Glu-Asn-2-(2-naphthyl)ethylamide,
Alloc-pAph-Glu-Asn-2-(1-naphthyl)ethylamide,
Alloc-pAph-Glu-Asn-2-(2-pyridyl)ethylamide,
Alloc-pAph-Glu-Asn-2,2-diphenylethylamide,
Alloc-pAph-Glu-Asn-2,4-difluorobenzylamide, and
Alloc-pAph-Glu-Asn-4-dimethylaminobenzylamide.

17. A compound, or a pharmaceutically acceptable salt, amide, or ester thereof, having the following formula:

Alloc-pAph-Glu-Arg-Cha-NH$_2$,
Allylaminocarbonyl-pAph-Glu-Arg-Cha-NH$_2$,
Alloc-pAph-Glu-Arg-Chg-NH$_2$,
Alloc-pAph-Glu-Dap[—C(=NH)—NH$_2$]-Cha-NH$_2$,
Alloc-pAph-Glu-Ala[3—C(=NH)—NH$_2$]-Cha-NH$_2$,
Alloc-pAph-Glu-Asn-Cha-NH$_2$,
Alloc-pAph-Glu-Dab-Cha-NH$_2$,
Alloc-pAph-Glu-Dap[—C(=NH)—NH$_2$]—NH$_2$,
Alloc-pAph-Glu-Gly-Cha-NH$_2$,
Alloc-pAph-Glu-Thr(Bzl)-NH—(CH$_2$)$_2$—CH(Ph)$_2$,
Alloc-pAph-Glu-Dab-NH—(CH$_2$)$_2$—Ph,
Alloc-pAph-Glu-Asn-NH—CH$_2$-Chx, Alloc-pAph-Glu-Dap[—C(=NH)—CH$_3$]-Cha-NH$_2$,
Alloc-pAph-Glu-Dab[—C(=NH)—NH$_2$]-Cha-NH$_2$,
Alloc-pAph-Glu-2-Abu(4-CN)-Cha-NH$_2$,
Alloc-pAph-Glu-Ala(3-CN)-Cha-NH$_2$,
Alloc-pAph-Glu-Asn-1-naphthylmethylamide,
Alloc-pAph-Glu-Asn-1-(1-naphthyl)ethylamide,
Alloc-pAph-Glu-Asn-2-naphthylmethylamide,
Alloc-pAph-Glu-Asn-3,4-dichlorobenzylamide,
Alloc-pAph-Glu-Asn-2-(3-chlorophenyl)ethylamide,
Alloc-pAph-Glu-Arg(NO$_2$)-Cha-NH$_2$,
Alloc-pAph-Glu-Cys(Bzl)-Cha-NH$_2$,
Alloc-pAph-Glu-Trp-Cha-NH$_2$,
Alloc-pAph-Glu-Phg-Cha-NH$_2$,
Alloc-pAph-Glu-Asn-9-fluorenylamide,
Alloc-pAph-Glu-Asn-3,5-bistrifluoromethylbenzylamide,
Alloc-pAph-Glu-Dap[—C(=NH)—NH$_2$]-Phe[4-C(—S—(CH$_2$)$_2$—S—)—Ph]—NH$_2$,
Alloc-pAph-Glu-Cys(Bzl)-Cha-NH$_2$,
Alloc-pAph-Glu-Thr(Bzl)-Cha-NH$_2$,
Alloc-pAph-Glu-Phe(4-NO$_2$)-Cha-NH$_2$,
Alloc-pAph-Glu-Asn-3,4-methylenedioxybenzylamide,
Alloc-pAph-Glu-Asn-2-(2-naphthyl)ethylamide,
Alloc-pAph-Glu-Asn-2-(1-naphthyl)ethylamide,
Alloc-pAph-Glu-Asn-2-(2-pyridyl)ethylamide,
Alloc-pAph-Glu-Asn-2,2-diphenylethylamide,
Alloc-pAph-Glu-Asn-2,4-difluorobenzylamide, and
Alloc-pAph-Glu-Asn-4-dimethylaminobenzylamide.

18. A process for the preparation of a compound as claimed in claim 1, which comprises the steps of:

(a1) coupling a compound of the formula Fmoc-E$_n$—OH wherein n is one, two, or three, to an acid sensitive linker attached to a resin, cleaving off the protecting group Fmoc, coupling a compound of the formula Fmoc-D1—D2—C(O)OH to the free amino group obtained, and again cleaving off the protecting group Fmoc, or for the preparation of a compound of the formula I in which n is zero, coupling a compound of the formula Fmoc-D1—D2—C(O)OH to an acid sensitive linker attached to a resin, and cleaving off the protecting group Fmoc;

(a2) coupling a compound of the formula Fmoc-B1—B2—C(O)OH to the free amino group obtained in step (a1) and cleaving off the protecting group Fmoc;

(a3) coupling a compound of the formula R1—A1—A2—C(O)OH to the free amino group obtained in step (a2); and (a4) cleaving off the compound obtained according to steps (a1) through (a3) from the resin by means of trifluoroacetic acid.

19. A process for the preparation of a compound as claimed in claim 1, which comprises the steps of:

(b1) coupling the side chain carboxylic acid of a compound of the formula Fmoc-B1—CHR97—C(O)OPG, wherein R97 is 2-hydroxycarbonylethyl and PG is a protecting group, to an acid sensitive benzylalcohol type of linker attached to an amino functionalized resin;

(b2) cleaving off the protecting group PG;

(b3) coupling a compound of the formula H$_2$N—D2—D3—E$_n$—R2, wherein n is zero, one, two, or three, to the free carboxylic acid obtained in step (b2);

(b4) cleaving off the protecting group Fmoc;

(b5) coupling a compound of the compound R1—A1—A2—C(O)OH to the free amino group obtained in step (b4); and, (b6) cleaving off the compound obtained according to steps (b1) through (b5) from the resin by means of trifluoroacetic acid.

20. A pharmaceutical composition comprising an effective amount of a compound as claimed in claim 1 and a pharmaceutically acceptable carrier.

21. A composition of matter comprising a prodrug of a compound as claimed in claim 1.

22. A composition of matter comprising an active metabolite of a compound as claimed in claim 1.

23. A method of inhibiting factor VIIa comprising contacting factor VIIa or a material containing factor VIIa with a compound as claimed in claim 1.

24. A method of inhibiting factor VIIa comprising administering to a patient in need thereof an effective amount of a compound as claimed in claim 1.

25. A method of inhibiting or reducing blood clotting, inflammatory response, thromboembolic diseases, or vascular restenosis compound comprising administering to a patient in need thereof an effective amount of a compound as claimed in claim 1.

\* \* \* \* \*